(12) United States Patent
Anantharamiah et al.

(10) Patent No.: US 8,084,423 B2
(45) Date of Patent: Dec. 27, 2011

(54) SYNTHETIC SINGLE DOMAIN POLYPEPTIDES MIMICKING APOLIPOPROTEIN E AND METHODS OF USE

(75) Inventors: Gattadahalli M. Anantharamiah, Birmingham, AL (US); David W. Garber, Birmingham, AL (US); Geeta Datta, Pelham, AL (US)

(73) Assignee: UAB Research Foundation, Birmingham, AL (US)

( * ) Notice: Subject to any disclaimer, the term of this patent is extended or adjusted under 35 U.S.C. 154(b) by 816 days.

(21) Appl. No.: 11/405,601

(22) Filed: Apr. 17, 2006

(65) Prior Publication Data

US 2007/0101448 A1 May 3, 2007

Related U.S. Application Data

(63) Continuation of application No. 10/712,447, filed on Nov. 13, 2003, now Pat. No. 7,563,771.

(60) Provisional application No. 60/425,821, filed on Nov. 13, 2002.

(51) Int. Cl.
*A61K 38/00* (2006.01)
*A61K 38/13* (2006.01)
*C07K 5/00* (2006.01)

(52) U.S. Cl. .......... 514/7.4; 514/1.1; 514/1.9; 514/16.4; 514/21.5; 530/300; 530/327; 530/402

(58) Field of Classification Search ........................ None
See application file for complete search history.

(56) References Cited

U.S. PATENT DOCUMENTS

| | | | |
|---|---|---|---|
| 4,877,611 | A | 10/1989 | Cantrell |
| 4,897,355 | A | 1/1990 | Eppstein et al. |
| 4,946,778 | A | 8/1990 | Ladner et al. |
| 5,579,250 | A | 11/1996 | Balaji et al. |
| 5,612,895 | A | 3/1997 | Balaji et al. |
| 5,631,280 | A | 5/1997 | Ciccarone et al. |
| 5,843,708 | A | 12/1998 | Hardman et al. |
| 5,877,153 | A | 3/1999 | Harris et al. |
| 6,107,457 | A | 8/2000 | Arlinghaus et al. |
| 6,113,898 | A | 9/2000 | Anderson et al. |
| 6,201,165 | B1 | 3/2001 | Grant et al. |
| 6,423,511 | B1 | 7/2002 | Nakamura et al. |
| 6,444,111 | B1 | 9/2002 | Montgomery |
| 6,458,592 | B1 | 10/2002 | Jakobovitz et al. |
| 6,472,184 | B1 | 10/2002 | Hegemann |
| 6,514,523 | B1 | 2/2003 | Sparks |
| 6,664,230 | B1 | 12/2003 | Fogelman et al. |
| 6,930,085 | B2 | 8/2005 | Fogelman et al. |
| 6,933,279 | B2 | 8/2005 | Fogelman et al. |
| 7,144,862 | B2 | 12/2006 | Fogelman et al. |
| 7,166,578 | B2 | 1/2007 | Fogelman et al. |
| 7,199,102 | B2 | 4/2007 | Fogelman et al. |
| 7,563,771 | B2 | 7/2009 | Anantharamiah et al. |
| 7,579,319 | B2 | 8/2009 | Fogelman et al. |
| 2004/0186057 | A1 | 9/2004 | Anantharamiah et al. |
| 2005/0164950 | A1 | 7/2005 | Fogelman et al. |
| 2007/0032430 | A1 | 2/2007 | Fogelman et al. |
| 2007/0254839 | A1 | 11/2007 | Fogelman et al. |

FOREIGN PATENT DOCUMENTS

| | | |
|---|---|---|
| WO | WO86/01533 | 3/1986 |
| WO | WO 01/75067 | 10/2001 |
| WO | WO 02/15923 | 2/2002 |
| WO | WO 03/086326 | 10/2003 |

OTHER PUBLICATIONS

Weers et al., Eur., J., Biochem., 2001, vol. 268: 3728-3735.*
Zaiou et al., J. Lipid Res., 2000, vol. 41:1087-1095.*
Qin et al., Circulation, 2006, vol. 114:II-110.*
Eck, S. L. and Wilson, J. M.,1996, in: Goodman & Gilman's The Pharmacological Basis of Therapeutics, Ninth Edition, McGraw-Hill, New York.*
Abrahmsen, et al. *Biochemistry* 30: 4151 (1991).
Alvarez and Curiel, *Hum. Gene Ther.*, 8:597-613 (1997).
Baggiolini, et al. *FEBS Lett.* 307: 97-101 (1992).
Beisiegel, et al. *Nature* 341: 162-164 (1989).
Brigham, et al. *Am. J. Resp. Cell. Mol. Biol.* 1:95-100 (1989).
Catapano, et al. *J. Biol. Chem.* 254: 1007-1009 (1979).
Clark-Lewis, et al. *Biochemistry* 30: 3128 (1991).
Crystal, *Hum. Gene Ther.*, 8: 985-1001 (1997).
Datta, et al. *Biochemistry* 30: 213-220 (2000).
Datta, et al., *Journal of Lipid Research* 42: 959-966 (2001).
Dashti, et al. *Journal of Lipid Res*. 45: 1919-1928 (2004).
Dawson, et al. *Science* 266: 776-779 (1994).
Deedwania, P.C. *Med. Clin. North Am.* 79: 973-998 (1995).
Eisenberg, et al. *J. Chin Invest*. 90: 2013-2021 (1992).
Felgner, et al. *PNAS*, 84: 7413-7417 (1987).
Garber, et al. *J. Lipid. Res*. 41: 1020-1026 (2000).
Gianturco, et al., *Journal of Lipid Research* 23: 984-993 (1982).
Havel, R. J. *Arteriosclerosis* 5: 569-580 (1985).
Hussain, et al. *J. Biol. Chem*. 275: 29324-29330 (2000).
Illingworth, et al. *Current Opini. Lipidol*. 10: 383-386 (1999).
Johnson, *Posttranslational Covalent Modification of Proteins*, Ed., Academic Press, New York, pp. 1-17 (1983).
Jones, et al. "Computer programs to identify and classify amphipathic of domains." *J. Lipid. Res*. 33: 287-296 (1992).
Kwiterovich, and Guyton *Am. J. Cardiol*. 82: U-7U (1998).
Linton and Fazio, *Curr. Opin. Lipidol*. 10: 97-105 (1999).
Mahley, et al. *J. Lipid Res*. 40: 622-630 (1999).
Marais, . *Curr. Opin. Lipidol*. 11: 597-602 (2000).
Miller, et al. *Mol. Cell. Biol*. 6: 2895 (1986).
Paka, et al. *J. Biol. Chem*. 274: 4816-4823 (1999).
Pastan, et al. *PNAS*, 85: 4486 (1988).
Rajarathnam, et al. *Biochemistry* 33: 6623-6630 (1994).
Ramprasad, et al. *J. Controlled Release*, 79: 207-218 (2002).
Schnolzer, et al. *Science* 256: 221 (1992).
Schonfeld, et al. *J. Clin. Invest*. 64: 1288-1297 (1979).
Segrest, et al. *Proteins: Structure, Function and Genetics*, 8: 103-117 (1990).

(Continued)

*Primary Examiner* — Elizabeth C Kemmerer
*Assistant Examiner* — Xiaozhen Xie
(74) *Attorney, Agent, or Firm* — Ballard Spahr LLP

(57) ABSTRACT

The present invention is directed to a synthetic apolipoprotein-E mimicking polypeptide consisting of a single domain. The invention is also directed to nucleic acid encoding the polypeptide, vectors including the nucleic acid, antibodies specific for the polypeptide, and compositions comprising the same and methods of using the same.

26 Claims, 12 Drawing Sheets

OTHER PUBLICATIONS

Segrest, et al. *Structure of the plasma lipoproteins in "Atlas of Atherosclerosis"* 2nd ed., edited by P.W.F. Wilson, p. 56 (2000).

Spira, et al. *J. Immun. Methods* 7: 307 (1984).

Steplewski, et al. *PNAS* 82: 8653 (1985).

Swarnakar, et al. *J. Biol. Chem.* 276: 21121-21126 (2001).

Tytler, et al. *J. Biol. Chem.* 268: 2212-2218 (1993).

Watts, et al. *Atherosclerosis* 141: 17-30 (1998).

Wigland et al. In: *Adenovirus DNA*, Martinus Nijhoff Publishing, Boston, 408-441 (1986).

Wilson et al. *Science* 252: 1817-1822 (1991).

Zaiou et al., *Journal of Lipid Research* 41: 1087-1095 (2000).

Datta G, White CR, Dashti N, Chaddha M, Palgunachari MN, Gupta H, Handattu SP, Garber DW, Anantharamaiah GM. (2009) Anti-inflammatory and recycling properties of an apolipoprotein mimetic peptide, Ac-hE18A-NH(2). Atherosclerosis Epub ahead of print. Volume and page TBA.

Garber DW, Handattu S, Aslan I, Datta G, Chaddha M, Anantharamaiah GM. (2003) Effect of an arginine-rich amphipathic helical peptide on plasma cholesterol in dyslipidemic mice. Atherosclerosis 168(2):229-237.

Anantharamaiah G, Navab M, Reddy ST, Garber DW, Datta G, Gupta H, White CR, Handattu SP, Palgunachari MN, Chaddha M, Mishra VK, Segrest JP, Fogelman AM. (2006) Synthetic peptides: managing lipid disorders. Curr Opin Lipidol. 17(3): 233-237.

Anantharamaiah GM, Mishra VK, Garber DW, Datta G, Handattu SP, Palgunachari MN, Chaddha M, Navab M, Reddy ST, Segrest JP, Fogelman AM. (2007) Structural requirements for antioxidative and anti-inflammatory properties of apolipoprotein A-I mimetic peptides. J Lipid Res. 48(9): 1915-1923.

Bechinger B. (2000) Understanding peptide interactions with the lipid bilayer: a guide to membrane protein engineering. Curr Opin Chem Biol. 4(6):639-644.

Blackburn WD Jr, Dohlman JG, Venkatachalapathi YV, Pillion DJ, Koopman WJ, Segrest JP, Anantharamaiah GM. (1991) Apolipoprotein A-I decreases neutrophil degranulation and superoxide production. J Lipid Res. 32(12): 1911-1918.

Charles-Schoeman C, Banquerigo ML, Hama S, Navab M, Park GS, Van Lenten BJ, Wagner AC, Fogelman AM, Brahn E. (2008) Treatment with an apolipoprotein A-1 mimetic peptide in combination with pravastatin inhibits collagen-induced arthritis. Clin Immunol. 127(2): 234-244.

Clark-Lewis I, Dewald B, Loetscher M, Moser B, Baggiolini M. (1994) Structural requirements for interleukin-8 function identified by design of analogs and CXC chemokine hybrids. J Biol Chem. 269(23): 16075-16081.

Epand RM, Stafford A, Leon B, Lock PE, Tytler EM, Segrest JP, Anantharamaiah GM. (1994) HDL and apolipoprotein A-I protect erythrocytes against the generation of procoagulant activity. Arterioscler Thromb. 14(11): 1775-1783.

Geysen HM, Mason TJ, Rodda SJ. (1988) Cognitive features of continuous antigenic determinants. J Mol Recognit. 1(1): 32-41.

Gupta H, Dai L, Datta G, Garber DW, Grenett H, Li Y, Mishra V, Palgunachari MN, Handattu S, Gianturco SH, Bradley WA, Anantharamaiah GM, White CR. (2005) Inhibition of lipopolysaccharide-induced inflammatory responses by an apolipoprotein AI mimetic peptide. Circ Res. 97(3): 236-243.

Gupta H, White CR, Handattu S, Garber DW, Datta G, Chaddha M, Dai L, Gianturco SH, Bradley WA, Anantharamaiah GM. (2005) Apolipoprotein E mimetic Peptide dramatically lowers plasma cholesterol and restores endothelial function in watanabe heritable hyperlipidemic rabbits. Circulation. 111(23): 3112-3118.

Kandel ER, Schwartz JH, Jessell TM (Eds.) (1991) Principles of Neural Science, Third Edition. Elsevier: New York, pp. 188-189.

Navab M, Anantharamaiah GM, Hama S, Garber DW, Chaddha M, Hough G, Lallone R, Fogelman AM. (2002) Oral administration of an Apo A-I mimetic Peptide synthesized from D-amino acids dramatically reduces atherosclerosis in mice independent of plasma cholesterol. Circulation. 105(3): 290-292.

Owens BJ, Anantharamaiah GM, Kahlon JB, Srinivas RV, Compans RW, Segrest JP. (1990) Apolipoprotein A-I and its amphipathic helix peptide analogues inhibit human immunodeficiency virus-induced syncytium formation. J Clin Invest. 86(4): 1142-1150.

Van Lenten BJ, Wagner AC, Anantharamaiah GM, Garber DW, Fishbein MC, Adhikary L, Nayak DP, Hama S, Navab M, Fogelman AM. (2002) Influenza infection promotes macrophage traffic into arteries of mice that is prevented by D-4F, an apolipoprotein A-I mimetic peptide. Circulation. 106(9): 1127-1132.

Wake AK, Datta G, Palgunachari MN, Mishra VK, Anantharamaiah GM, White RG. Apolipoprotein A-1 mimetic peptide retains function after oxidant expolsure. Proc ASME 2008 Summer Bioenginerring Conference (Marco Island, Florida), Jun. 25-29, 2008, SBC2008-189660.

Weers PM, Narayanaswami V, Ryan RO. (2001) Modulation of the lipid binding properties of the N-terminal domain of human apolipoprotein E3. Eur J Biochem. 268(13): 3728-3735.

Zhang Z, Datta G, Mishra VK, Anantharamaiah GM, White CR. (2007) D-4F, An Apolipoprotein A-I Mimetic Peptide, Prevents Endothelial Dysfunction Induced by Myeloperoxidase-Derived Hypochlorous Acid. Meeting Abstract 21: 706.11, FASEB J.

* cited by examiner

R14 L-1

R14-L2

Bilayer

Cylindric

Micellar

Inverted cone

Hexagonal ($H_{II}$)

Cone

US 8,084,423 B2

SYNTHETIC SINGLE DOMAIN POLYPEPTIDES MIMICKING APOLIPOPROTEIN E AND METHODS OF USE

This application is a continuation and claims benefit of U.S. Ser. No. 10/712,447, filed Nov. 13, 2003, now U.S. Pat. No. 7,563,771, which application is hereby incorporated herein by reference. U.S. Ser. No. 10/712,447 claims priority of 60/425,821, which was filed Nov. 13, 2002.

FIELD OF THE INVENTION

This invention relates to the field of molecular biology and protein biology including polypeptides and polypeptide mimics. This application also relates to the field of cholesterol metabolism, catabolism and the treatment and management of cholesterol associated conditions.

COPYRIGHT NOTIFICATION

Pursuant to 37 C.F.R. §1.71(e), a portion of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

Plasma lipoproteins and Coronary artery disease. Epidemiological studies indicate that increased plasma cholesterol levels increase the risk for atherosclerosis. Five completed major trials have provided conclusive evidence of a benefit from treatment aimed primarily at reducing low-density lipoprotein (LDL) -cholesterol (Illingworth R. D., et al. *Current Opini. Lipidol.* 1999, 10:383-386). Among other lipoprotein risk factors is familial dysbetalipoproteinemia, which results in the accumulation of remnant atherogenic lipoproteins derived from the catabolism of chylomicron and VLDL (Kwiterovich, P. O., Jr. *Am. J. Cardiol.* 1998, 82:3U-7U). It has been shown that a 1% decrease in the plasma cholesterol level decreases the risk of coronary artery disease by 2% (Deedwania, P. C. *Med. Clin. North Am.* 1995, 79:973-998). The focus of angiographic trials has been on LDL reduction and these studies have demonstrated that decreases of LDL-cholesterol of more than 30% to 35% are associated with lower rates of coronary events (Watts, G. W., et al. *Atherosclerosis* 1998, 414:17-30). There is also growing evidence that triglyceride-rich lipoproteins may adversely affect endothelial function and increase oxidative stress by promoting the production of small, dense LDL and by reducing high-density lipoprotein (HDL) levels (Marais, D., *Curr. Opin. Lipidol.* 2000, 11:597-602).

Anti-atherogenic properties of Apolipoprotein E (Apo E). Apolipoprotein E is a protein that binds lipid and has two major domains (Mahley, R. W., et al. *J. Lipid Res.* 1999, 40:622-630). The 22 kDa amino terminal domain has been shown by X-ray crystallographic studies to be a 4-helix bundle (Wilson, C., et al. *Science* 1991;252:1817-1822) and to contain a positively-charged receptor binding domain. For this region to mediate very low-density lipoprotein (VLDL) binding to its receptors, the apolipoprotein must associate with the lipoprotein surface; this is enabled by the C-terminal amphipathic helical region. If the 4-helix bundle that contains the positively charged receptor-binding domain does not open up on the lipoprotein surface, then the VLDL is defective in binding to receptors. Thus, the positively charged arginine (Arg)-rich cluster domain of the Apo E and the C-terminal amphipathic helical domain, are both required for the enhanced uptake of atherogenic Apo E-containing lipoproteins.

Chylomicron is a lipoprotein found in blood plasma, which carries lipids from the intestines into other body tissues and is made up of a drop of triacylglycerols surrounded by a protein-phospholipid coating. Chylomicron remnants are taken up by the liver (Havel, R. J., 1985, *Arteriosclerosis.* 5:569-580) after sequestration in the space of Disse, which is enriched with Apo E (Kwiterovich, P. O., Jr., 1998; Deedwania, P. C., 1995; and Watts, G. W., et al., 1998). Apo E is the major mediator of hepatic remnant lipoprotein uptake by the LDL receptor or LRP. Lipolysis of normal VLDL Sf (subfraction) of more than 60 permit binding of the lipolytic remnant to the LDL receptor (Catapano, A. L. et al. 1979, *J. Biol. Chem.* 254:1007-1009; Schonfield, G., et al. 1979. *J. Clin. Invest.* 64:1288-1297). Lipoprotein lipase (LpL) may facilitate uptake through localization of Apo B-containing lipoproteins to membrane heparan sulphate proteoglycan (HSPG) (Eisenberg, et al. 1992. *J. Clin. Invest.* 90:2013-2021; Hussain, M., et al., *J. Biol. Chem.* 2000, 275:29324-29330) and/or through binding to the LDL-receptor-related protein (LRP) (Beisiegel, U., et al., 1989, *Nature* 341:162-164). Cell-surface HSPG may also function as a receptor and has variable binding affinities for specific isoforms of Apo E. In particular, Apo E is synthesized by the liver and also by monocyte/macrophages, where it exerts its effect on cholesterol homeostasis. In vivo evidence for the local effect of lack of Apo E comes from the observations of Linton and Fazio, who showed accelerated atherosclerosis in C57BL/6 mice transplanted with bone marrow from Apo E-deficient mice (Linton, M. F. and Fazio, S. *Curr. Openi. Lipidol.* 1999, 10:97-105). Apo E-dependent LDL cholesteryl ester uptake pathway has been demonstrated in murine adrenocortical cells (Swarnakar, S., et al. *J. Biol. Chem.* 2001, 276:21121-21126). This appears to involve chondroitin sulphate proteoglycan (CSPG) and a 2-macroglobulin receptor.

It has been shown that the receptor-binding domain of Apo E, rich in Arg residues (141-150), covalently linked to a synthetic class A amphipathic-helical domain, enhances the hepatic atherogenic lipoprotein uptake (Datta, G. et al. *Biochemistry* 2000, 30:213-220). Recent studies indicate that a potential anti-atherogenic action of Apo E is that it stimulates endothelial production of heparan sulfate (HS) (Paka, L., et al. *J. Biol. Chem.* 1999, 274:4816-4823). Lipoproteins are complexes of one or more lipids bound to one or more proteins and transport water-insoluble fats in the blood. Cholesterol is carried through the bloodstream by lipoproteins. There are no agents available which reduce cholesterol via the binding mechanisms of lipoproteins. There is a need for more effective agents that are capable of reducing cholesterol in a subject so as to reduce diseases and conditions which are associated with increased cholesterol.

SUMMARY OF THE INVENTION

The present invention provides polypeptides, compositions and methods for increasing uptake of cholesterol in a subject.

In one aspect, the invention is directed to a synthetic apolipoprotein-E mimicking polypeptide comprising consecutive amino acids having an amino acid sequence selected from the group of (i) X-Y-Arg-Arg-Y-Y-X-X-Y-Y-Arg-Y-Y-Arg-X-Y-Y-X or the reverse sequence thereof, (ii) Arg-Arg-Y-Y-

X-X-Y-Y-Arg-Y-Y-Arg-X-Y or the reverse sequence thereof, (iii) Y-Y-X-X-Y-Y-Arg-Y-Y-Arg-X-Y-Y-X or the reverse sequence thereof, and (iv) X-Y-Arg-Arg-Y-Y-X-X-Y-Y-Arg-Y-Y-Arg or the reverse sequence thereof, wherein X is glycine, threonine, serine or alanine, wherein Y is a hydrophobic amino acid, wherein the polypeptide comprises an acetyl group at the N-terminus and an amide group at the C-terminus, and wherein the polypeptide consists of a single domain.

In one embodiment of the polypeptide of the invention, Y is selected from the group consisting of phenylalanine, tyrosine, leucine, isoleucine, valine, and tryptophan. In another embodiment, the polypeptide comprises from about 10 amino acids to about 30 amino acids in length. In other embodiments, the invention provides a polypeptide comprising a sequence of consecutive amino acids selected from the group consisting of SEQ ID NOS:1-207. The invention also provides a specific embodiment wherein the polypeptide comprises the sequence Gly-Ile-Arg-Arg-Phe-Leu-Gly-Ser-Ile-Trp-Arg-Phe-Ile-Arg-Ala-Phe-Tyr-Gly (SEQ ID NO:5). In other embodiments, the polypeptide comprises a recombinant polypeptide, a synthetic polypeptide, and/or a peptidomimetic.

The present invention also provides peptides, which are capable of reducing cholesterol in subjects. In other aspects, the invention is also directed to compositions including the polypeptide and methods of using the polypeptide to reduce serum cholesterol in a subject.

In a specific aspect, the invention provides a composition comprising a nucleic acid encoding a peptide of the invention. In another aspect, the invention provides a composition comprising a peptide of the invention, wherein the composition is a protein. In one embodiment, the composition comprises a peptide which is encoded by a nucleic acid. In another embodiment, the nucleic acid is encoded in a vector. In a specific embodiment, the composition further comprises a pharmaceutically acceptable carrier. In another embodiment, the composition comprises an adjuvant.

The invention also provides, in another aspect, methods of increasing the effectiveness of the composition comprising a peptide of the invention, by combining the composition with an adjuvant.

In still another aspect, the invention provides an isolated nucleic acid encoding the polypeptide of the invention. In some embodiments, the nucleic acid comprises DNA, RNA and/or cDNA. In another aspect, the invention provides a vector comprising the nucleic acid. The invention also provides a host cell comprising the nucleic acid of the invention. In one embodiment, the cell is eukaryotic or prokaryotic.

Additionally, the invention provides a peptide that enhances low-density lipoprotein (LDL) binding and very low-density lipoprotein (VLDL) binding to a cell and/or that enhances low-density lipoprotein (LDL) and very low-density lipoprotein (VLDL) degradation by a cell.

In another aspect, the invention provides a composition comprising a polypeptide according to the invention and a pharmaceutically acceptable carrier. In a specific embodiment, the carrier comprises dimyristoylphosphatidyl (DMPC), phosphate buffered saline, a time release formulation or a multivesicular liposome.

In another aspect, the invention provides methods of increasing the solubility of the composition of the invention, comprising combining the composition with a solubilizing agent.

In yet another aspect, the invention provides a monoclonal antibody that specifically binds to the Apo E-derived polypeptide of the invention.

In still another aspect, the invention provides a composition including a recombinant cell expressing the nucleic acid encoding the peptide of the invention and a carrier. In addition, the invention provides a composition comprising a recombinant cell producing the polypeptide and a carrier.

The invention also provides a transgenic non-human subject expressing the nucleic acid according to the invention. In one embodiment, the subject is an animal or a plant. In another embodiment, the transgenic non-human subject synthesizes and/or produces the polypeptide.

The invention provides methods for using the peptides of the invention. In one aspect, the invention provides a method for enhancing LDL binding to and/or uptake by a cell, the method comprising mixing, contacting and/or associating the cell with the polypeptide of the invention, thereby allowing the polypeptide to bind the LDL and enhance LDL binding and/or uptake with the associated cell. In another aspect, the invention provides a method for enhancing LDL binding and VLDL binding to a cell in a subject. The method comprises administering the polypeptide, or a composition thereof, to the subject in an amount effective to increase LDL and VLDL binding to the cell of the subject.

Also provided are methods of reducing serum cholesterol in a patient. In one aspect, the method comprises administering to the patient a composition comprising a peptide of the invention, wherein the peptide enhances cellular uptake of cholesterol in the patient, thereby reducing the patient's serum cholesterol. In another aspect, the invention provides a method for reducing serum cholesterol in a subject, the method comprising the step of administering to the subject an amount of the polypeptide or a composition thereof, effective to increase binding of LDL and/or VLDL to cells in the subject, thereby reducing serum cholesterol in the subject.

In still another aspect, the invention provides methods of enhancing LDL uptake in a patient, comprising administering to the patient a composition comprising a peptide of the invention, wherein the composition enhances cellular uptake of LDL in the patient and thereby enhances LDL uptake in the patient.

The invention also provides methods of enhancing VLDL uptake in a patient, comprising administering to the patient a composition comprising a peptide of the invention, wherein the composition enhances cellular uptake of VLDL in the patient and thereby enhances VLDL uptake in the patient.

In another aspect, the invention provides for a method of treating a subject with a disease or condition associated with high serum cholesterol, comprising administering to the subject an amount of the polypeptide of the invention effective to reduce serum cholesterol, thereby ameliorating the disease or condition.

In yet another aspect, the invention provides for a method for treating a subject with coronary artery disease, the method comprising the step of administering to the subject an amount of the polypeptide, or a composition thereof, effective to increase cellular uptake of serum cholesterol in the subject to thereby treat the subject. In one embodiment, the disease or condition associated with high serum cholesterol is dysbetalipoproteinemia.

In still another aspect, the invention provides a method for reducing the risk of myocardial infarction in a subject, the method comprising the step of administering to the subject an amount of the polypeptide, or a composition thereof, effective to increase cellular uptake of serum cholesterol in the subject, to thereby reduce the risk of myocardial infarction in the subject.

In another aspect, the invention provides a method of reducing a blockage in the circulatory system of a patient comprising administering to the patient a composition comprising the polypeptide of the invention in an amount effective to increase uptake of cholesterol in the subject so as to reduce the blockage in the circulatory system of the patient. In one embodiment, the composition is administered directly to the location of the blockage in the subject. In another embodiment, the composition is administered to a patient in combination with a thrombolytic agent, such as aspirin.

The invention also provides methods of breaking an embolus in a patient comprising administering to the patient a composition comprising a peptide of the invention in an amount effective to increase uptake of cholesterol in the subject so as to break an embolus in the patient.

In another aspect, the invention provides for a method for treating atherosclerosis in a subject, the method comprising the step of administering the to subject an amount of a polypeptide or a composition of the invention effective to bind serum cholesterol and/or enhance cellular uptake of serum cholesterol in the subject, thereby treating atherosclerosis in the subject. In addition, the invention provides a method for reducing plaque formation on vessel walls.

In yet another embodiment, the invention provides methods of reducing the risk of a stroke in a patient comprising administering to the patient a composition comprising a peptide of the invention in an amount effective to increase cellular uptake of cholesterol in the patient and thereby reduce the risk of stroke in the patient.

In addition, the invention provides methods of reducing the risk of myocardial infarction in a patient comprising administering to the patient the composition comprising a peptide of the invention in an amount effective to increase cellular uptake of cholesterol in the patient and thereby reduce the risk of myocardial infarction in the patient.

In yet another aspect, the invention provides for use of the polypeptide for the making of a composition to treat a disease associated with increased serum cholesterol in a subject. In still another aspect, the invention provides for use of the polypeptide for the making of a composition to reduce LDL and/or VLDL serum levels in a subject.

BRIEF DESCRIPTION OF THE DRAWINGS

The accompanying drawings, which are incorporated in and constitute a part of this specification, illustrate several embodiments of the invention and together with the description, serve to explain the principles of the invention. These are non-limiting examples.

DETAILED DESCRIPTION OF THE INVENTION

Figures 1A, 1B, 1C, 1D, 1E, 1F:
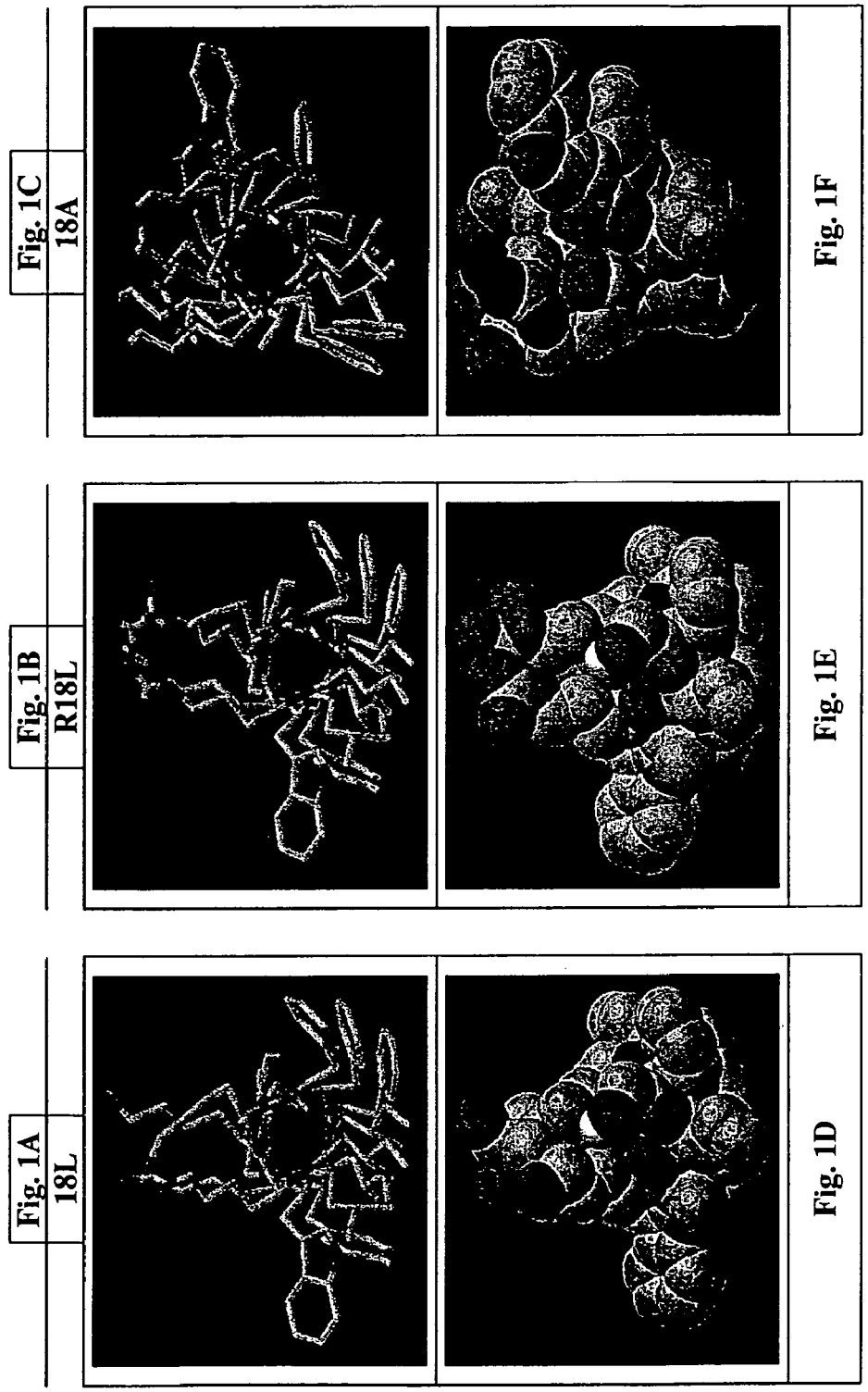
FIGS. 1A-1F are representations of space-filling molecular models of the 18L peptide, the R-18L peptide and the 18A peptide developed to study the cross-sectional shape of these molecules. Space filling models (FIGS. 1D, 1E and 1F) are shown along with the approximate cross sectional shape (FIGS. 1A, 1B and 1C). The cross sectional molecular shapes presented here show the cross-sectional area of the head groups versus the fatty acyl chains of the synthetic peptide analogs of the invention.

All patents, patent applications and publications cited herein, whether supra or infra, are hereby incorporated by reference in their entireties into this application in order to more fully describe the state of the art as known to those skilled therein as of the date of the invention described and claimed herein.

It is to be understood that this invention is not limited to specific synthetic methods, or to specific recombinant biotechnology methods unless otherwise specified, or to particular reagents unless otherwise specified, to specific pharmaceutical carriers, or to particular pharmaceutical formulations or administration regimens, as such may, of course, vary. It is also to be understood that the terminology used herein is for the purpose of describing particular embodiments only and is not intended to be limiting.

Definitions and Nomenclature

The terminology used herein is for the purpose of describing particular embodiments only and is not intended to be limiting.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q glutamine; R, arginine; S, serine; T, threonine; V, valine; W, tryptophan; Y, tyrosine; Z, glutamine or glutamic acid.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristoylation, oxidation, pergylation, proteolytic processing, phosphorylation, prenylation, racemization, selenoylation, sulfation, and transfer-RNA mediated addition of amino acids to protein such as arginylation. (See *Proteins—Structure and Molecular Properties* 2nd Ed., T. E. Creighton, W. H. Freeman and Company, New York (1993); *Posttranslational Covalent Modification of Proteins*, B. C. Johnson, Ed., Academic Press, New York, pp. 1-12 (1983)).

As used herein, the term "amino acid sequence" refers to a list of abbreviations, letters, characters or words representing amino acid residues.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof As used herein, "reverse analog" or "reverse sequence" refers to a peptide having the reverse amino acid sequence as another, reference, peptide. For example, if one peptide has the amino acid sequence ABCDE, its reverse analog or a peptide having its reverse sequence is as follows: EDCBA.

Compounds and Compositions of the Invention

The present invention is directed to a synthetic apolipoprotein-E mimicking peptide or polypeptide. The polypeptide may comprise an amino acid sequence selected from the group of (i) X-Y-Arg-Arg-Y-Y-X-X-Y-Y-Arg-Y-Y-Arg-X-Y-Y-X, or the reverse sequence thereof, (ii) Arg-Arg-Y-Y-X-X-Y-Y-Arg-Y-Y-Arg-X-Y, or the reverse sequence thereof, (iii) Y-Y-X-X-Y-Y-Arg-Y-Y-Arg-X-Y-Y-X, or the reverse sequence thereof, and (iv) X-Y-Arg-Arg-Y-Y-X-X-Y-Y-Arg-Y-Y-Arg, or the reverse sequence thereof, where X is glycine, threonine, serine or alanine, where Y is a hydrophobic amino acid, where the polypeptide comprises an acetyl group at the N-terminus and an amide group at the C-terminus, and where the polypeptide consists of a single domain.

In one embodiment, Y is selected from the group consisting of phenylalanine, tyrosine, leucine, isoleucine, valine, tryptophan, and combinations thereof. In another embodiment, the polypeptide comprises from about 10 amino acids to about 30 amino acids in length. In a further embodiment, the peptide of the invention comprises from about 14 amino acids to about 18 amino acids. The peptide of the invention can be about 14 amino acids in length or about 18 amino acids in length. In a further embodiment, the polypeptide comprises a sequence of consecutive amino acids selected from the group of SEQ ID NOS:1-207. In another embodiment, the polypeptide comprises the sequence Gly-Ile-Arg-Arg-Phe-Leu-Gly-Ser-Ile-Trp-Arg-Phe-Ile-Arg-Ala-Phe-Tyr-Gly (SEQ ID NO:5). In a further embodiment, the polypeptide comprises a recombinant polypeptide. In another embodiment, the polypeptide comprises a synthetic polypeptide. In another embodiment, the polypeptide comprises a peptidomimetic.

The invention also provides a polypeptide that enhances low-density lipoprotein (LDL)—and very low density lipoprotein (VLDL)—binding to a cell. In one embodiment, the polypeptide enhances low-density lipoprotein (LDL)—and very low density lipoprotein (VLDL)—degradation by a cell. In addition, the invention provides a mixture of one or more of the peptides described herein, wherein the mixture of peptides is administered to a subject to reduce cholesterol in the subject.

Non-limiting Examples of Polypeptides and Peptides of the Invention

Non-limiting examples of peptides of the invention are given below. A number of possible analogs of class L peptides ranging from about 18 amino acids to about 10 amino acids in length were synthesized using art-recognized methods. The peptides are protected at the N-terminus by an acetyl group and at the C-terminus by an amide group. Table 1 shows non-limiting examples of peptides that are analogs or reverse analogs of the 18L peptide which have an increased angle subtended by its helix.

TABLE 1

| Amino Acid Sequence | SEQ ID NO: |
| --- | --- |
| GIRRFLGSIWRFIRAFYG- | 13 |
| GIWRFLGSIRRFIRAFYG | 14 |
| GIGRFLRSIWGFIRAFYR | 15 |
| GIRRFLGSIWRFIGAFYR | 16 |
| GIRRFLGSIWAFIRRFYG | 17 |
| GIRRFLSGIWRFIRAFYG | 18 |
| GIRRFLSGIWAFIRAFYG | 19 |
| GIWRFLSGIRRFIRAFYG | 20 |
| GIRRFLGAIWRFIRSFYG | 21 |
| GIWRFLGAIWRFIRSFYG | 22 |
| Reverse analogs (reverse amino acid sequence of the above peptides) | |
| GYFARIFRWISGLFRRIG | 23 |
| GYFARIFRRISGLFRWIG | 24 |
| RYFARIFGWISRLFRGIG | 25 |
| RYFAGIFRWISRLFRGIG | 26 |
| GYFRRIFAWISGLFRRIG | 27 |
| GYFARIFRWIGSLFRRIG | 28 |

TABLE 1-continued

| Amino Acid Sequence | SEQ ID NO: |
| --- | --- |
| GYFARIFRWIGSLFRRIG | 29 |
| GYFRRIFRRIGSLFAWIG | 30 |
| GYFSRIFRWIAGLFRRIG | 31 |
| GYFSRIFRWIAGLFRWIG | 32 |

Table 2 shows non-limiting examples of DiMet-lysine analogs and reverse analogs of peptides.

TABLE 2

| Amino Acid Sequence of Analogs, wherein K' + (DiMe)Lys | SEQ ID NO: |
| --- | --- |
| GIK'K'FLGWIK'AFISK'FYG | 33 |
| GIWK.FLGSIK'K'FIK'AFYG | 34 |
| GIGK'FLK'SIWGFIK'AFYK' | 35 |
| GIK'K'FLGSIWK'FIGAFYK' | 36 |
| GIK'K'FLGSIWAFIK'K'FYG | 37 |
| GIK'K'FLSGIWK'FIK'AFYG | 38 |
| GIK'K'FLSGIWFIAK'K'FYG | 39 |
| GIWK'FLSGIK'K'FIK'AFYG | 40 |
| GIK'K'FLGAIWK'FIK'SFYG | 41 |
| GIWK'FLGAIK'K'FIK'SFYG | 42 |
| Reverse analogs | |
| GYFAK'IFK'WISGLFK'K'IG | 43 |
| GYFAK'IFK'K'ISGLFK'WIG | 44 |
| K'YFAK'IFGWISK'LFK'GIG | 45 |
| K'YFAGIFK'WISK'LFK'GIG | 46 |
| GYFK'K'IFAWISGLFK'K'IG | 47 |
| GYFAK'IFK'WIGSLFK'K'IG | 48 |
| GYFAK'IFK'WIGSLFK'K'IG | 49 |
| GYFK'K'IFK'K'IGSLFAWIG | 50 |
| GYFSK'IFK'WIAGLFK'K'IG | 51 |
| GYFSK'IFK'K'IAGLFK'WIG | 52 |

Table 3 shows non-limiting examples of polypeptides of the invention having enhanced solubility.

TABLE 3

| Amino Acid Sequence | SEQ ID NO: |
| --- | --- |
| GIK'RFLGSIWRFIK'AFYG | 53 |
| GIWK'FLGSIRRFIK'AFYG | 54 |
| GIGK'FLRSIWGFIRAFYK' | 55 |
| GIK'RFLGSIWRFIGAFYK' | 56 |

TABLE 3-continued

| Amino Acid Sequence | SEQ ID NO: |
|---|---|
| GIRK'FLGSIWAFIK'RFYG | 57 |
| GIRK'FLSGIWRFIK'AFYG | 58 |
| GIRK'FLSGIWAFIK'AFYG | 59 |
| GIWK'FLSGIRRFIK'AFYG | 60 |
| GIK'RFLGAIWRFIK'SFYG | 61 |
| GIWK'FLGAIWRFIK'SFYG | 62 |
| Reverse analogs | |
| GIK'RFLGWIK'AFISRFYG | 63 |
| GYFAK'IFRWISGLFK'RIG | 64 |
| GYFAK'IFRRISGLFK'WIG | 65 |
| RYFAK'IFGWISRLFK'GIG | 66 |
| RYFAGIFK'WISRLFK'GIG | 67 |
| GYFRK'IFAWISGLFK'RIG | 68 |
| GYFAK'IFRWIGSLFK'RIG | 69 |
| GYFAK'IFRWIGSLFRK'IG | 70 |
| GYFK'RIFRK'IGSLFAWIG | 71 |
| GYFSK'IFRWIAGLFK'RIG | 72 |
| GYFSRIFRWIAGLFRWIG | 73 |

In one embodiment, the amino acid sequence of a polypeptide of the invention is varied with regard to the ratio of arginine compared to dimethyl-lysine. For example, a peptide is synthesized with one to three arginine residues per peptide. Table 4 shows non-limiting examples of such analogs and reverse analogs.

TABLE 4

| Amino acid sequence | SEQ ID NO: | Reverse analogs | SEQ ID NO. |
|---|---|---|---|
| GIRKFLGSIWRFIKAFYG (2Lys and 2Arg analog of 18L) | 74 | GYFARIFKWISGLFRKIG | 83 |
| GIWKFLGSIRRFIKAFYG | 75 | GYFARIFKRISGLFKWIG | 84 |
| GIGRFLKSIWGFIRAFYK | 76 | RYFAKIFGWISKLFRGIG | 85 |
| GIRKFLGSIWRFIGAFYK | 77 | RYFAGIFRWISRLFRGIG | 86 |
| GIRKFLGSIWAFIRKFYG | 78 | GYFKRIFAWISGLFKRIG | 87 |
| GIRKFLSGIWRFIKAFYG | 79 | GYFAKIFRWIGSLFKRIG | 88 |
| GIRKFLSGIWRFIKAFYG | 80 | GYFAKIFRWIGSLFKRIG | 89 |
| GIWKFLSGIRRFIKAFYG | 81 | GYFKRIFRKIGSLFAWIG | 90 |
| GIRKFLGAIWRFIKSFYG | 82 | GYFARIFRWISGLFKRIG | 101 |
| GIRKFLGSIWRFIRAFYG (1Lys and 3Arg analog of 18L) | 91 | GYFARIFRKISGLFRWIG | 102 |
| GIWRFLGSIKRFIRAFYG | 92 | RYFARIFGWISKLFRGIG | 103 |
| GIGRFLKSIWGFIRAFYR | 93 | KYFAGIFRWISRLFRGIG | 104 |
| GIRRFLGSIWKFIGAFYR | 94 | GYFKRIFAWISGLFRRIG | 105 |
| GIRRFLGSIWAFIKRFYG | 95 | GYFAKIFRWIGSLFRRIG | 106 |
| GIRRFLSGIWRFIKAFYG | 96 | GYFAKIFRWIGSLFRRIG | 107 |
| GIRKFLSGIWAFIRAFYG | 97 | GYFRKIFRRIGSLFAWIG | 108 |
| GIWRFLSGIKRFIRAFYG | 98 | GYFSKIFRWIAGLFRRIG | 109 |
| GIRKFLGAIWRFIRSFYG | 99 | GIRRILGSFWRFFRAIYG | 110 |
| GIWRFLGAIWKFIRSFYG | 100 | | |

Table 5 shows non-limiting examples of peptides of the invention, the analogs having aromatic amino acids substituted with hydrophobic amino acids.

TABLE 5

| Amino Acid Sequence | SEQ ID NO: |
|---|---|
| GFRRILGSFWRIFRAIYG | 111 |
| GFRRILGSIWRFIRAFYG | 112 |
| GIRRFLGSIWRIFRAFYG | 113 |
| GIRRFLGSFWRIIRAFYG | 114 |
| GLRRFIGSIWRFIRAFYG | 115 |
| GLRRFIGSIWRFIRAFYG | 116 |
| GIRRFIGSIWRFLRAFYG | 117 |
| GIRRFLGSFWRIFRAIYG | 118 |
| GFRRFLGSFWRIIRAIYG | 119 |
| GIRRFLGSIYRFIRAFWG | 120 |
| GIRRFYGSIWRFIRAFLG | 121 |
| GYIARFIRWFSGLIRRFG | 122 |
| GYGARIFRWISGLIRRFG | 123 |
| GYFARFIRWISGLFRRIG | 124 |
| GYFARIFRWISGIFRRLG | 125 |
| GYIARIFRWFSGLFRRIG | 126 |

Table 6 shows non-limiting examples of peptides of the invention with enhanced helicity. In these examples, Ile residues are replaced by Leu residues (helix promoting) to enhance helicity. In particular, the Ile pushes the alkyl chain apart in the helix structure due to branching at C-, in contrast to Leu side chain.

TABLE 6

| Amino Acid Sequence | SEQ ID NO: |
|---|---|
| GLRRFIGSLWRFLRAFYG | 127 |
| GYFARLFRWLSGIFRRLG | 128 |

TABLE 6-continued

| Amino Acid Sequence | SEQ ID NO: |
|---|---|
| GIRRFLGSLWRFLRAFYG | 129 |
| GYFARLFRWLSFLFRRIG | 130 |
| GLRRFLGSIWRFLRAFYG | 131 |
| GYFARLFRWISGLFRRLG | 132 |

Table 7 shows non-limiting examples of peptides of the invention having a shorter length relative to other peptides of the invention having their N-terminal 2 to 4 amino acids deleted and C-terminal 2 to 4 amino acids deleted.

TABLE 7

| Amino Acid Sequence | SEQ ID NO: | Amino Acid Sequence | SEQ ID NO: |
|---|---|---|---|
| GIRRFYGSIWRFIR | 133 | RFIRWISGYFRRIG | 151 |
| RIFRWISGYFRRIG | 134 | RIFRWISGYIRRFG | 152 |
| RRFYGSIWRFIRAF | 135 | RIFRWISGYFRRLG | 153 |
| FARIFRWISGYFRR | 136 | RLFRWISGYFRRIG | 154 |
| GLRRFYGSLWRFLR | 137 | GIRRFYGSIWRFLR | 155 |
| RLFRWLSGYFRRLG | 138 | GLRRFYGSIWRFIR | 156 |
| RRFYGSLWRFLRAF | 139 | GIRRFYGSLWRFIR | 157 |
| FARLFRWLSGYFRR | 140 | GIRRYFGSIWRFIR | 158 |
| GIRRFYGSIWRFLR | 141 | GIRRYFGSLWRFLR | 159 |
| RLFRWISGYFRRIG | 142 | GIRRYFGSLWRFIR | 160 |
| RRFYGSIWRFLRAF | 143 | RIFRWISGFYRRIG | 161 |
| FARLFRWISGYFRR | 144 | RLFRWISGFYRRLG | 162 |
| GIRRFYGSLWRFLR | 145 | RIFRWLSGFYRRIG | 163 |
| RLFRWISGYFRRLG | 146 | RLFRWLSGFYRRIG | 164 |
| RREYGSIWRFLRAF | 147 | RFLRWISGFYRRIG | 165 |
| FARIFRWLSGYFRR | 148 | RFLRWISGFYRRIG | 166 |
| GFRRIYGSIWRFIR | 149 | GFRRLYGSIWRFIR | 167 |
| GIRRFYGSIWRIFR | 150 | GIRREYGSIWRIFR | 168 |

Table 8 shows non-limiting examples of peptides of the invention with varying Lysine (K) to Arginine (R) residue ratio: 3R and 1K.

TABLE 8

| Amino Acid Sequence | SEQ ID NO: | Amino Acid Sequence | SEQ ID NO: |
|---|---|---|---|
| GIKRFYGSIWRFIR | 169 | RFIRWISGYFRKIG | 187 |
| RIFRWISGYFRKIG | 170 | RIFKWISGYIRRFG | 188 |
| RKFYGSIWRFIRAF | 171 | RIFRWISGYFRKLG | 189 |
| FARIFRWISGYFKR | 172 | KLFRWISGYFRRIG | 190 |
| GLKRFYGSLWRFLR | 173 | GIRRFYGSIWKFLR | 191 |
| RLFRWLSGYFRKLG | 174 | GLKRFYGSIWRFIR | 192 |
| RKFYGSLWRFLRAF | 175 | GIRRFYGSLWKFIR | 193 |
| FARLFRWLSGYFKR | 176 | GIRRYFGSLWRFIR | 194 |
| GIKRFYGSIWRFLR | 177 | GLRRYFGSIWRFLR | 195 |
| RLFRWISGYFRKIG | 178 | GIRRYFSGLWRFIR | 196 |
| RKFYGSIWRFLRAF | 179 | RFLRWISGFYRRIG | 197 |
| FARLFRWISGYFKR | 180 | RLFRWISGFYRRLG | 198 |
| GIRKFYGSLWRFLR | 181 | RFLRWLSGFYRRIG | 199 |
| RLFKWISGYFRRLG | 182 | RLIRWLSGFYRRFG | 200 |
| RRFYGSIWRFLKAF | 183 | RFLRWFSGYIRRIG | 201 |
| FAKIFRWLSGYFRR | 184 | RFLRWISGYFRRIG | 202 |
| GFRRIYGSIWRFIK | 185 | GFRRLYSGIWRFIR | 203 |
| GIRKFYGSIWRIFR | 186 | GIRRYFGSIWRIFR | 204 |

Further non-limiting examples of the peptides of the invention include peptides with an increased angle subtended, such as GIRRFLGWIRAFISRFVG-Arg (analog of 18L) (SEQ ID NO:205); a peptide with an increased angle DiMe-K—GIK'K'FLGWIK'AFISK'FVG, wherein K'=DiMe-K (SEQ ID NO:206); and peptides with an enhanced solubility, such as GIK'RFLGWIK'AFISRFVG (SEQ ID NO:207).

Numerous variants or derivatives of the peptides and analogs of the invention are also contemplated. Non-limiting examples of the peptides and analogs thereof have been described herein (see Tables 1-8, for example). As used herein, the term "analog" is used interchangeably with "variant" and "derivative." Variants and derivatives are well understood to those of skill in the art and can involve amino acid sequence modifications. Such, amino acid sequence modifications typically fall into one or more of three classes: substantial; insertional; or deletional variants. Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Substitutions, deletions, insertions or any combination thereof may be combined to arrive at a final derivative or analog. Substitutional variants are those in which at least one residue has been removed and a different residue inserted in its place. Such substitutions generally are made in accordance with Table 9 and are referred to as conservative substitutions.

TABLE 9

Amino Acid Substitutions

| Original Residue | Non-limiting Exemplary Conservative Substitutions |
|---|---|
| Ala | Ser |
| Arg | Gly, Gln |
| Asn | Gln; His |
| Asp | Glu |
| Cys | Ser |
| Gln | Asn, Lys |
| Glu | Asp |
| Gly | Ala |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 9, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions which in general are expected to produce the greatest changes in the protein properties are those in which: (a) the hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or hystidyl, is substituted for (or by) an electronegative residue, e.g. glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

It is understood that one way to define the variants and derivatives of the disclosed proteins herein is to define them in terms of homology/identity to specific known sequences. Specifically disclosed are variants of anti-atherogenic peptides and other proteins or peptides herein disclosed which have at least, 70% or at least 75% or at least 80% or at least 85% or at least 90% or at least 95% homology to the known sequence, such as Apo E. Those of skill in the art readily understand how to determine the homology of two proteins.

Polypeptide Production—Polypeptides of the invention are produced by any method known in the art. One method of producing the disclosed polypeptides is to link two or more amino acid residues, peptides or polypeptides together by protein chemistry techniques. For example, peptides or polypeptides are chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). A peptide or polypeptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively, (Grant G A (1992) *Synthetic Peptides: A User Guide*. W.H. Freeman and Co., New York (1992); Bodansky M and Trost B., Ed. (1993) *Principles of Peptide Synthesis*. Springer-Verlag Inc., New York). Alternatively, the peptide or polypeptide is independently synthesized in vivo. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two-step chemical reaction (Dawson et al. *Science*, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolim M et al. (1992) *FEBS Lett*. 307:97-101; Clark-Lewis I et al., *J. Biol. Chem.*, 269:16075 (1994); Clark-Lewis I et al., *Biochem.*, 30:3128 (1991); Rajarathnam K et al., *Biochem*. 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV*. Academic Press, New York, pp. 257-267 (1992)).

Nucleic Acid and Vectors—The invention is also directed to an isolated nucleic acid encoding any one or more of the polypeptides disclosed herein. In one embodiment, the nucleic acid comprises DNA, RNA and/or cDNA. It would be routine for one with ordinary skill in the art to make a nucleic acid that encodes the polypeptides disclosed herein since codons for each of the amino acids that make up the polypeptides are known. As non-limiting examples, the nucleic acids of the invention can be produced by recombinant, in vitro methods, or by chemical synthetic means using machines and standard chemistry which would be known to one of skill in the art, or by in vivo cellular synthesis. Methods of synthesizing nucleic acids would be well know to one of skill in the art. For example, U.S. Pat. No. 6,472,184 to Hegemann, issued Oct. 29, 2002, entitled "Method for producing nucleic acid polymers" and U.S. Pat. No. 6,444,111 to Montgomery, issued Sep. 3, 2002, entitled "Electrochemical solid phase synthesis of polymers describes such synthesis" describe such synthetic methods. These references are hereby incorporated by reference in their entireties.

Additionally, the invention provides a vector comprising the nucleic acid encoding any one or more of the polypeptides and peptides described herein. In certain embodiments, the invention provides a vector comprising a nucleic acid encoding at least one of the peptides of the present invention, e.g., at least one of SEQ ID NOS:1-207. The vector can be a viral vector, a plasmid vector, a cosmid vector, an adenoviral vector, a phage vector, a retroviral vector, an adeno-associated viral (AAV) vector, or any other vector capable of including a nucleic acid encoding a peptide or polypeptide of the invention. The vector can be an expression vector that is intended and capable of integrating into a cell genome. Other useful virus vectors include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses. Useful vectors and their construction are disclosed in Sambrook, J. Fritsch, E F, and Maniatis, T. (1989) *Molecular Cloning: A Laboratory Manual* (2nd ed.), Cold Spring Harbor Laboratory Press, Plainview, N.Y.

Host cell—The invention also provides for a host cell containing the nucleic acid, polypeptide, peptide, and/or the vector of the invention. Such a host cell is a eukaryotic cell or a prokaryotic cell. In the case of eukaryotic cells, retrovirus or adenovirus based vectors can be used to put the nucleic acid or the invention into the host cell. Methods known to one of skill in the art to insert the nucleic acids or polypeptides in host cells are encompassed within this invention. The following are non-limiting examples of such methods: naked DNA transfection, lipofectin-mediated transfer, transformation, micro-injection of nucleic acid into a cell, or calcium-phosphate precipitation tranfection methods. Host cells can be obtained from commercial sources such as the American Type Culture Collection (ATCC). Host cells can be grown in liquid media culture or on tissue culture plates. The growth conditions will be dependent upon the specific host cells used and such conditions would be known to one of skill in the art. Tranfection and growth of host cells is described in Maniatis, et al., id. The invention provides for a recombinant cell expressing a nucleic acid encoding the polypeptide of the claimed invention. The invention also provides for a recombinant cell producing the polypeptide of the invention.

The vectors used in the host cells contain all or a part of a viral genome, such as long term repeats ("LTRs"), promoters (e.g., CMV promoters, SV40 promoter, RSV promoter), enhancers, and so forth. A non-limiting example of such adenoviruses which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: *Adenovirus DNA*, Doerfler, Ed., Martinus Nijhoff Publishing, Boston, pp. 408-441 (1986)). When the host cell is a prokaryote, bacterial viruses, or phages, can be used to deliver the nucleic acid of the invention to the host cell. A non-limiting example of such vectors are vectors based upon, e.g., lambda phage. In any case, the vector may comprise elements of more than one virus. The vector may additionally comprise a gene encoding a marker or reporter molecule to more easily trace expression of the vector.

Antibodies—The invention also provides polyclonal and monoclonal antibodies that bind the peptides and polypeptides in the invention. For example, monoclonal antibody is also provided that specifically binds to the Apo E-derived polypeptides of the invention. In some embodiments, the monoclonal antibody specifically binds to a polypeptide having an amino acid sequence of any one or more of SEQ ID NOS:1-207. One of ordinary skill in the art knows how to make or produce monoclonal antibodies, which specifically bind to a polypeptide having a known amino acid sequence. (See for example, Steplewski et al., 1985, *Proc. Natl. Acad. Sci. USA* 82:8653; Spira et al., 1984, *J. Immunological Methods* 74:307, PCT Publication WO 86/01533 (1986) and U.S. Pat. No. 6,458,592.) The monoclonal antibody, in some embodiments, can be chimeric (e.g., U.S. Pat. No. 5,843,708 to Hardman, et al., Dec. 1, 1998, entitled "Chimeric antibodies"), humanized (e.g., U.S. Pat. No. 6,423,511 to Nakamura, et al., issued Jul. 23, 2002, entitled "Humanized antibodies"), primatized (e.g., U.S. Pat. No. 6,113,898 to Anderson, et al., issued Sep. 5, 2000, entitled "Human B7.1-specific primatized antibodies and transfectomas expressing said antibodies"), and/or linked to other polypeptides as fusion proteins. Portions of the monoclonal antibody can also be useful, either alone or linked to other proteins. These portions include, but are not limited to Fab (Fab')$_2$, Fv, etc. In another embodiment, the monoclonal antibody can be linked to a carrier (e.g., water, buffered water, 0.4% saline, 0.3% glycine, and the like) or can be associated with an adjuvant (e.g., biliverdin, bilirubin, biotin, carnosine, chitin, etc.). Adjuvants have been used experimentally to promote a generalized increase in immunity against unknown antigens (e.g., U.S. Pat. No. 4,877,611).

For preparation of monoclonal antibodies, any technique which provides antibodies produced by continuous cell line cultures can be used. Examples include the hybridoma technique (Kohler and Milstein (1975), *Nature,* 256:495-497, the disclosure of which is incorporated herein by reference), the trioma technique, the human B-cell hybridoma technique (Kozbor et al. (1983), *Immunol. Today* 4:72, and the EBV-hybridoma technique (Cole et al. (1985), in *Monoclonal Antibodies and Cancer Therapy*, Alan R. Liss, Inc., pp. 77-96). Techniques described for the production of single chain antibodies (U.S. Pat. No. 4,946,778), can be adapted to produce single chain antibodies to the polypeptides of the invention. Alternatively, transgenic mice may be used to express humanized antibodies to these polypeptides or fragments.

Any of the procedures described above may be used to detect antibody binding. One such screening assay is described in "Methods for Measuring Cellulase Activities", *Meth. In Enzymol.,* 160:87-116.

Compositions—The invention provides for a composition comprising any one or more of the polypeptides, nucleic acids, vectors and/or antibodies described herein can be used to produce a composition of the invention which may also include a carrier such as a pharmaceutically acceptable carrier.

The polypeptide, nucleic acid, vector, or antibody of the invention can be in solution or in suspension (for example, incorporated into microparticles, liposomes, or cells). These compositions can be targeted to a particular cell type via antibodies, receptors, or receptor ligands. One of skill in the art knows how to make and use such targeting agents with the compositions of the invention. A targeting agent can be a vehicle such as an antibody conjugated liposomes, receptor mediated targeting of DNA through cell specific ligands, and highly specific retroviral targeting of cells in vivo. Any such vehicles can be part of the composition of the invention. In general, receptors are involved in pathways of endocytosis, either constitutive or ligand induced. These receptors cluster in clathrin-coated pits, enter the cell via clatrhin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, ligand valency, and ligand concentration.

In one embodiment, the composite comprises pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: *The Science and Practice of Pharmacy* (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semipermeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions may also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium choloride solution, Ringer's dextrose, dextrose and sodium choloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

Transgenic Subjects—The invention also provides for a transgenic, non-human subject expressing a nucleic acid of the invention encoding a polypeptide or peptide of the invention. In one embodiment, the subject is an animal or a plant. The invention also provides for a transgenic non-human subject expressing the polypeptide of the invention.

The animals can be produced by the process of transfecting a cell within the animal with any of the nucleic acid molecules disclosed herein. Methods for producing transgenic animals would be known to one of skill in the art, e.g., U.S. Pat. No. 6,201,165, to Grant, et al., issued Mar. 13, 2001, entitled "Transgenic animal models for cardiac hypertrophy and methods of use thereof." In non-limiting embodiments, the animal is a mammal, and the mammal is mouse, rat, rabbit, cow, sheep, pig, or primate, such as a human, monkey, ape, chimpanzee, or orangutan. The invention also provides an animal produced by the process of adding to such animal (for example, during an embryonic state) any of the cells disclosed herein.

Compositions (such as vectors) and methods are provided, which can be used for targeted gene disruption and modification to produce the polypeptides of the invention in any animal that can undergo gene disruption. Gene modification and gene disruption refer to the methods, techniques, and compositions that surround the selective removal or alteration of a gene or stretch of chromosome in an animal, such as a mammal, in a way that propagates the modification through the germ line of the mammal. In general, a cell is transformed with a vector, which is designed to homologously recombine with a region of a particular chromosome contained within the cell, as for example, described herein. This homologous recombination event can produce a chromosome which has exogenous DNA introduced, for example in frame, with the surrounding DNA. This type of protocol allows for very specific mutations, such as point mutations or the insertion of DNA to encode for a new polypeptide, to be introduced into the genome contained within the cell. Methods for performing this type of homologous recombination are known to one of skill in the art.

Once a genetically engineered cell is produced through the methods described above, an animal can be produced from this cell through either stem cell technology or cloning technology. For example, if the cell into which the nucleic acid was transfected was a stem cell for the organism, then this cell, after transfection and culturing, can be used to produce a transgenic organism which will contain the gene modification or disruption in germ line cells, which can then in turn be used to produce another animal that possesses the gene modification or disruption in all of its cells. In other methods for production of an animal containing the gene modification or disruption in all of its cells, cloning technologies can be used. These technologies are known to one of skill in the art and generally take the nucleus of the transfected cell and either through fusion or replacement fuse the transfected nucleus with an oocyte, which can then be manipulated to produce an animal. The advantage of procedures that use cloning instead of ES technology is that cells other than ES cells can be transfected. For example, a fibroblast cell, which is very easy to culture and can be used as the cell in this example, which is transfected and has a gene modification or disruption event take place, and then cells derived from this cell can be used to clone a whole animal.

Disclosed are nucleic acids used to modify a gene of interest that is cloned into a vector designed for example, for homologous recombination.

Methods for Making the Compositions of the Invention. The compositions disclosed herein and the compositions necessary to perform the disclosed methods can be made using any method known to those of skill in the art for that particular reagent or compound unless otherwise specifically noted. For example, there are a variety of methods that can be used for making these compositions, such as synthetic chemical methods and standard molecular biology methods.

The peptide, polypeptides, nucleic acids and vectors of the invention can be used to make certain other aspects of the invention. For example, the peptides and polypeptides of the invention can be used to produce the antibodies of the invention. Nucleic acids and vectors of the invention can be used to produce the peptides and polypeptides and other recombinant proteins of the invention. Host cells of the invention can be used to make nucleic acids, proteins, peptides, antibodies, and transgenic animals of the invention. These synthetic methods are described above.

As described above, the polypeptides or peptides of the invention may also be used to generate antibodies, which bind specifically to the polypeptides or fragments of the polypeptides. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention, sequences substantially identical thereto, or fragments of the foregoing sequences.

In immunoaffinity procedures, the antibody is attached to a solid support, such as a bead or column matrix. The protein preparation is placed in contact with the antibody under conditions under which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

The antibodies of the invention can be attached to solid supports and used to immobilize apolipoprotein E or polypeptides of the present invention. Polyclonal antibodies generated against the polypeptides of the invention can be obtained by direct injection of the polypeptides into an animal or by administering the polypeptides to an animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

Methods of Use

The invention also provides many therapeutic methods of using the nucleic acids, peptides, polypeptides, vectors, and antibodies, and compositions of the invention.

For example, the invention provides a method for enhancing LDL binding to a cell, the method comprising contacting, mixing or associating the cell with the polypeptide, thereby allowing the polypeptide to bind the LDL and enhance LDL binding and/or uptake with the associated cell. Also provided is a method for enhancing LDL and VLDL binding to a cell in a subject, the method comprising administering the polypeptide of the invention, or a composition thereof, to the subject in an amount effective to increase LDL and VLDL binding to the cell of the subject.

Further, the invention additionally provides a method for reducing serum cholesterol in a subject. In this method, an amount of the polypeptide of the invention, or a composition thereof, is administered to a subject in an amount effective to increase binding of LDL and/or VLDL to cells in the subject and enhance cellular uptake of serum cholesterol, thereby reducing serum cholesterol in the subject.

The invention also provides a method for treating a subject with coronary artery disease or any disease or condition associated with increased serum cholesterol. In this method, an amount of the polypeptide of the invention, or a composition thereof, is administered to the subject in an amount to effectively enhance cellular uptake of serum cholesterol in the subject and thereby treat the coronary artery disease or other associated disease in the subject. For example, the associated disease or condition can be dysbetalipoproteinemia, high blood pressure, atherosclerosis, angina, etc. Diseases or conditions associated with increased serum cholesterol would be well known to one of ordinary skill in the art.

In addition, the invention provides for a method for reducing the risk of myocardial infarction in a subject. In this method, an amount of the polypeptide of the invention, or a composition thereof, is administered to the subject in an amount effective to increase cellular uptake of serum cholesterol in the subject, to thereby treat the subject and reduce risk of myocardial infarction. The invention also provides a method for treating atherosclerosis in a subject, where an effective amount of the composition of the invention is administered to subject to increase cellular uptake of serum cholesterol and to thereby treat the atherosclerosis in the subject.

The invention also provides for the use of the polypeptide of the invention for the making of a composition of the invention, for example, to treat a disease associated with increased serum cholesterol in a subject or to reduce LDL and/or VLDL serum levels in a subject. Such a subject may be a mammal, such as a human. In another embodiment, the subject is an animal which can be a model system used to test human therapeutics. Non-limiting examples of such animals include dog, pig, primate, murine, feline, bovine, or equine animals.

For delivery of the nucleic acids of the invention to a cell, either in vitro or in vivo, a number of direct delivery systems can be used. These include liposome fusion, gene gun injection, endocytosis, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject. Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

The present invention provides polypeptides, which can be delivered (administered) to a subject in many different ways. For example, the peptides or nucleic acids encoding the peptides can be delivered to a subject during an angioplasty or other medical procedure. The peptides can be expressed in a plant (via transgenic technology) and the plant material can be ingested by the subject.

Infection of cells of a subject using a nucleic acid, vector, or composition of the invention can be carried out in vitro or in vivo. In vitro infection of cells can be carried out by adding the gene transfer vectors to the cell culture medium. When infection is carried out in vivo, the solution containing the gene transfer vectors may be administered by a variety of modes, depending on the tissue, which is to be infected. Examples of such modes of administration include injection of gene transfer vectors into the skin, topical application onto the skin, direct application to a surface of epithelium, or instillation into an organ (e.g., time release patch or capsule below the skin or into a tumor). The delivery mechanism chosen will depend in part on the type of cell targeted and whether the delivery is occurring for example in vivo or in vitro.

Thus, the compositions can comprise, liposomes, such as cationic liposomes (e.g., DOTMA, DOPE, DC-cholesterol) or anionic liposomes. Furthermore, liposomes comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see e.g., Brigham et al., *Am. J. Resp. Cell. Mol. Biol.* 1:95-100 (1989); Felgner et al., *Proc. Natl. Acad. Sci USA* 84:7413-7417 (1987); and U.S. Pat. No. 4,897,355. Furthermore, the polypeptides or nucleic acids of the invention can be administered as a component of a microcapsule that can be targeted to specific cell types, such as vessel wall cells, or where the diffusion of the compound or delivery of the compound from the microcapsule is designed for a specific rate or dosage.

As one example, vector delivery can be via a viral system, such as a retroviral vector system which can package a recombinant retroviral genome (see, e.g., Pastan et al., *Proc. Natl. Acad. Sci U.S.A.* 85:4486, 1988; or Miller et al., *Mol. Cell. Biol.* 6:2895, 1986). The recombinant retrovirus is then used to infect and thereby deliver to the infected cells nucleic acid encoding the polypeptide of the invention. For example, if a nucleic acid disclosed herein is delivered to the cells of a subject in an adenovirus vector, the dosage for administration of adenovirus to humans can range from about 107 to 109 plaque forming units (pfu) per injection but can be as high as 1012 pfu per injection (Crystal, *Hum. Gene Ther.* 8:985-1001, 1997; Alvarez and Curiel, *Hum. Gene Ther.* 8:597-613, 1997). A subject can receive a single dose or injection of the composition or polypeptide, or, if additional doses are necessary, they can be repeated at some time interval, such as one hour, one day, one week, one month, or other appropriate time intervals, as determined by the skilled practitioner, for an indefinite period and/or until the efficacy of the treatment has been established.

Nucleic acids that are delivered to cells, which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. Those of skill in the art know these systems, and the methods necessary to promote homologous recombination.

Therapeutic Uses

In general, when used for treatmenat, the therapeutic compositions may be administered orally, parenterally (e.g., intravenously or subcutaneous administration), by intramuscular injection, by intraperitoneal injection, transdermally, extracorporeally, by intracavity administration, transdermally, or topically or the like, including topical intranasal administration or administration by inhalant. The topical administration can be ophthalmically, vaginally, rectally, or intranasally. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular nucleic acid or vector used, its mode of administration and the like. An appropriate amount for a particular composition and a particular subject can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. Parenteral administration includes use of a slow release, a time release or a sustained release system such that a constant dosage is maintained.

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products. Following administration of a disclosed composition, such as a peptide, for treating, inhibiting, or preventing artherosclerosis, the efficacy of the therapeutic peptide can be assessed in various ways well known to the skilled practitioner. For instance, one of ordinary skill in the art will understand that a composition, such as a peptide, disclosed herein is efficacious in treating or inhibiting artherosclerosis in a subject by observing that the composition reduces cholesterol, LDL, or VLDL levels or reduces the amount of cholesterol present in an assay, as disclosed herein. The compositions that inhibit increased cholesterol levels, LDL levels, VLDL levels artherosclerosis, or embolus formation as disclosed herein may be administered prophylactically to patients or subjects who are at risk for artherosclerosis, stroke, myocardial infarction, or embolus formation.

The peptides, polypeptides, nucleic acids, antibodies, vectors and therapeutic compositions of the invention can be combined with other well-known therapies and prophylactic vaccines already in use. The compositions of the invention can be used in combination with drugs used to stabilize the patient and limit damage to the heart. Such drugs include thrombolytics, aspirin, anticoagulants, painkillers and tranquilizers, beta-blockers, ace-inhibitors, nitrates, rhythm-stabilizing drugs, and diuretics. Drugs that limit damage to the heart work only if given within a few hours of the heart attack. Thrombolytic drugs that break up blood clots and enable oxygen-rich blood to flow through the blocked artery increase the patient's chance of survival if given as soon as possible after the heart attack. Thrombolytics given within a few hours after a heart attack are the most effective. Injected intravenously, these include anisoylated plasminogen streptokinase activator complex (APSAC) or anistreplase, recombinant tissue-type plasminogen activator (r-tPA), and streptokinase. The compositions of the invention can be combined with any of these drugs. The combination of the peptides of the invention can generate an additive or a synergistic effect with current treatments.

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

NON-LIMITING EXAMPLES OF THE INVENTION

Example 1

Single Amphipathic Helical Structure Containing Arg Residue on Polar Face of Helix Associates with Lipid and Enhances Lipid Uptake The molecular modeling shown in FIGS. 1A-1F was performed to determine the nature of the helical structure of the single domain peptide of the invention given changes to the residues internal to the helix. Computer software useful to carry out the molecular modeling includes programs called WHEEL, LOCATE, HELNET described in M. K. Jones, G. M. Anantharamaiah, and J. P. Segrest; "Computer programs to identify and classify amphipathic α helical domains" *J. Lipid Res.* 33:287-296, 1992.

Experiments were designed to determine whether modulation of the atherogenic lipoprotein surface with positively charged residues would alter LDL binding to cell surface proteoglycans and lipoprotein uptake by the cells. Peptides were synthesized to alter residues on the atherogenic lipoprotein surface by increasing the positively charged residues there. Sequence specificity is not required in the Arg-rich domain of the dual-domain peptides for enhanced uptake of atherogenic lipoproteins. This invention provides that a single amphipathic-helical structure containing at least one Arg residue on the polar face of the amphipathic helix also associates with atherogenic LDL and VLDL and remnant lipoproteins to enhance their hepatic uptake and degradation. The positively-charged amphipathic helical peptides were tested with regard to altering heparin sulfate (HS) levels using cell culture systems.

In particular, the alteration of the residues in the helical single domain peptide was carried out. Biologically active amphipathic helices have been classified into several classes (Segrest, J. P. et al. *Proteins: Structure, function and Genetics* 8:103-117 (1990)). While the class A amphipathic helix stabilizes cell membranes, class L peptides destabilize (Tytler, E. M., et al. *J. Biol. Chem.* 268:2212-2218, 1993) and lyse cells. The entire polar face of class L amphipathic helix consists of Lys residues. Class L peptides possess a wide hydrophobic face and interact avidly with phospholipids, but due to their inverted wedge shape (FIGS. 1A-1F), they promote hex-phase formation, i.e., inverted micelle formation (or fusion process, see FIGS. 12A-12F). In FIGS. 1A-1F, the Lys residues are snorkeled. That is, the alkyl chains of Lys are going from a hydrophobic environment to an aqueous environment with the $\epsilon$-NH$_2$ of Lys exposed to water (imagine an elephant swimming with it trying to push its trunk exposed to air and the rest of the body in water) to a maximum extent and the molecules are energy minimized using the Sybyl program. FIGS. 1A and 1D show the 18L peptide; FIGS. 1B and 1E show the R-18L peptide; FIGS. 1C and 1F show the 18A peptide. The amino acid sequence of the 18L peptide is Ac-GIKKFLGSIWKFIWKFIKAYG-NH$_2$ (SEQ ID NO:1), the amino acid sequence of the R-18L peptide is Ac-GIRRFLG-SIWRFIRAFYG-NH$_2$ (SEQ ID NO:2) and the amino acid sequence of the 18A peptide is Ac-DWLKAFYDKVAEK-LKEAF-NH2 (SEQ ID NO:3). In FIGS. 12A-12F, inverted cone shaped phospholipids are shown (such as lyso PC), similar to 18A form micellar structures, and cone shaped phospholipids are shown (such as phosphatidylethanolamine, similar to 18L form inverted nonbilayer or hexagonal phase, an intermediate to fusion process in cells. FIGS. 1A-1F show peptide cross sectional structures and the corresponding lipid structures (FIGS. 12A-12F) can be correlated to these peptide structures. (J. P. Segrest, et al., *Structure of the plasma lipoproteins* in "*Atlas of Atherosclerosis*" Second Edition, edited by P. W. F Wilson, page 56, 2000). The peptides form cross sectional shapes similar to lipids as shown in FIGS. 12A-12F and thus, it is shown herein that amphipathic helical peptides with different cross sectional shapes possess different properties. For example, the dimethylation of the 18L peptide caused the peptide to become nonlytic. Similarly, the lytic activity of 18L is lost by changing Lys residues to Arg and the peptide can then be used for associating with atherogenic lipoproteins and allowing enhanced uptake of atherogenic lipoproteins by the liver. As shown in FIGS. 12A-12F, the tendency of phospholipids to form various types of aggregated structures is determined by the relative cross-sectional areas of the head groups versus the fatty acyl chains and, to a lesser extent, the length of the fatty acyl chains. Cone-shaped phospholipids, such as lysophospholipids and many detergents (wedge-shaped in cross-section), contain a relatively large polar head group and a single fatty acyl chain and favor a positive surface curvature and the micellar phase (i.e., a spheroidal particle). A lipoprotein particle is an example of a micelle formed from several different lipids and proteins. Cylindric-shaped phospholipids (e.g., phosphatidylcholine) are those whose head groups and fatty acyl chains have approximately equal cross-sectional areas and favor a flat surface, the membrane bilayer phase. Inverted cone-shaped phospholipids (inverted wedge-shaped in cross-section) include phosphatidylethanolamine; these contain relatively large acyl chain cross-sectional areas favoring a negative surface curvature and inverted nonbilayer phases. See FIGS. 12A-12F.

Accordingly, it was deduced and understood based on these molecular modeling experiments that a lytic peptide can be made non-lytic by increasing the width of the polar face either by substituting Lys with Arg or by dimethylating Lys residues. This is supported by the results shown in FIG. 2 and described in Example 2 that follows.

Example 2

Dimethylation of Lysine in the 18L Peptide Neutralizes the Hemolytic Property of the 18L Peptide This example was performed to test the affect of amino acid residue changes on the lytic nature of peptides of the invention. Lysine residues, which resided on the polar face of the single domain peptide, were substituted with arginine and such altered peptides were tested for lytic ability. Similarly, in other peptides of the invention, lysine residues on the polar face of the single domain peptide of the invention were dimethylated. These altered peptides neutralized the hemolytic property of the 18 L peptide. A suspension of erythrocytes (106 cells/ml) in phosphate-buffered saline with and without peptide (10 ml of 100 mM peptide solution) was incubated for 10 min at 37° C. Hemolysis was expressed as hemoglobin content (absorbance at 540 nm) of the supernatant after centrifugation at 16,000×g for 3 min. Hemoglobin content as measured in the presence of 0.1% Triton X-100 was taken as 100% hemolysis. Results indicated that while the 18L peptide was 80% lytic, DiMe18L peptide and R-18L peptide, similar to membrane stabilizing 18A peptide, did not cause lysis.

As shown in these experiments, the invention provides that a positively charged single amphipathic helical domain associates with atherogenic lipoproteins and enhances their hepatic uptake and degradation. However, it is important to eliminate the cytotoxic effects of the 18L peptide. For accomplishing this elimination of cytotoxic effects, knowing that the Arginine side chain exerts increased bulkiness to the side chain of this amino acid (similar to the dimethylation of Lys residues), an analog of the 18L peptide in which all Lys residues were replaced by Arg was synthesized. This was the first time that the effect of association of such peptides to atherogenic apo B-containing lipoproteins was appreciated.

Figure 2:
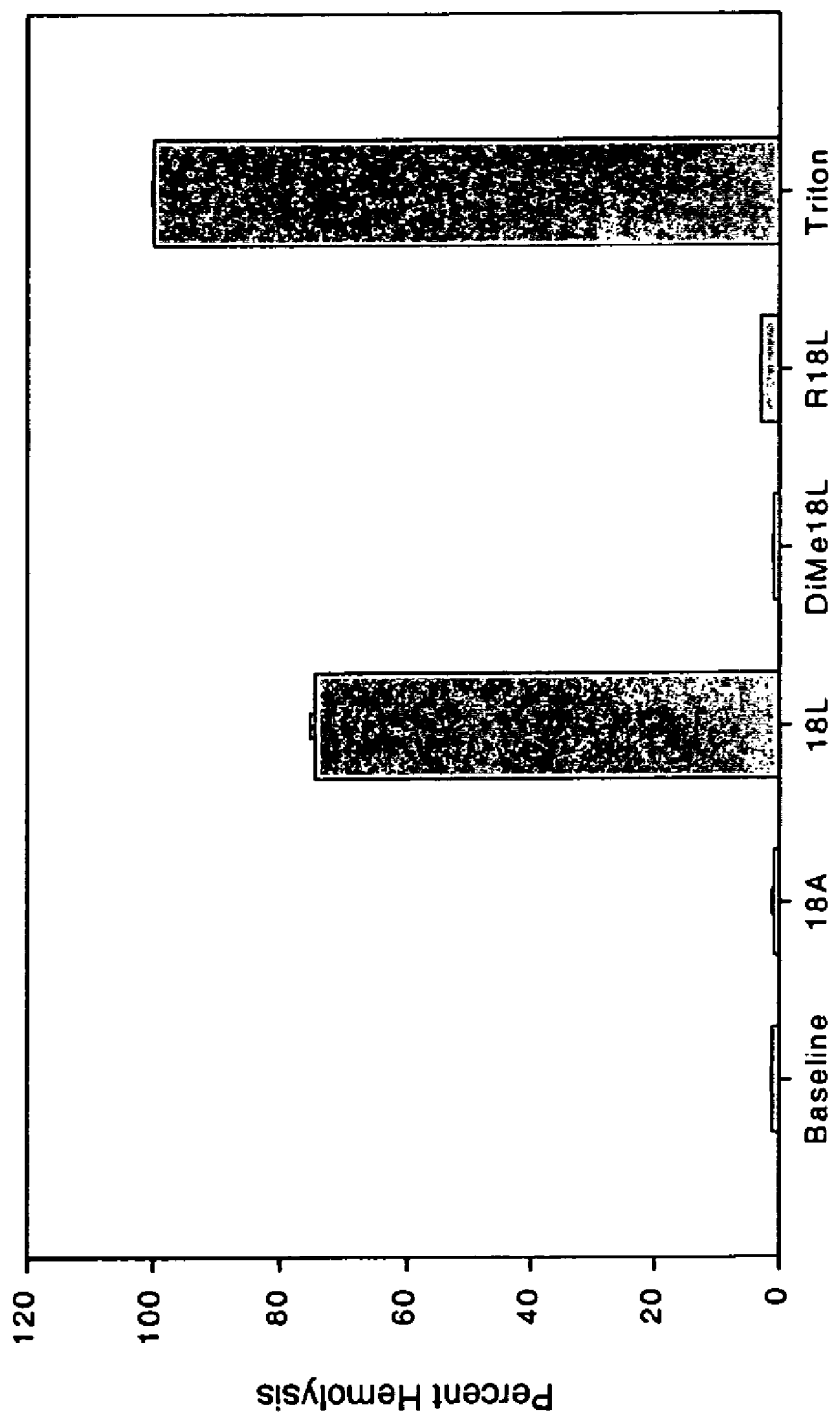
FIG. 2 is a graphic representation showing the effect of the 18A peptide, the 18L peptide, the R-18L peptide and the dimethyl-lysine (DiMeK) 18L polypeptides on red blood cells as measured by percent hemolysis.

In sum, this example shows that addition of the 18L peptide to red cells causes hemolysis (FIG. 2). However, dimethylation of Lys residues neutralizes the hemolytic property that is characteristic of class L peptide (FIG. 2). While the 18A peptide, the (DiMeK)18L peptide and the R-18L peptide do not cause cell lysis, the 18L peptide caused marked hemolysis as shown in FIG. 2.

The sequence of the 18L peptide is GIKKFLGSIWK-FIKAFVG (SEQ ID NO:7) which is a Class L amphipathic helix. The sequence of the (R)18L is GIRRFLGSIWR-FIRAFYG (SEQ ID NO:8) which is a class L amphipathic helix with the lysine residues changed to arginine. The sequence of the 18A peptide is DWLKAFYDKVAEK-LAEAF (SEQ ID NO:9) which is a class A amphipathic helix.

The 18L analog peptide with all lysine residues replaced by arginine ((R)18L) is also completely devoid of any hemolytic properties (FIG. 2). Circular dichroism (CD) resulted in the presence of lipid (DMPC) and indicated that peptides 18L, R-18L and Ac-18A-NH$_2$, all possesses comparable helicities. Model building indicated that the replacement of lysine in the 18L peptide by arginine residues transformed the inverted wedge cross-sectional shaped molecule into a trapezoidal shaped molecule (FIGS. 1A-1F).

Example 3

Figure 8A:
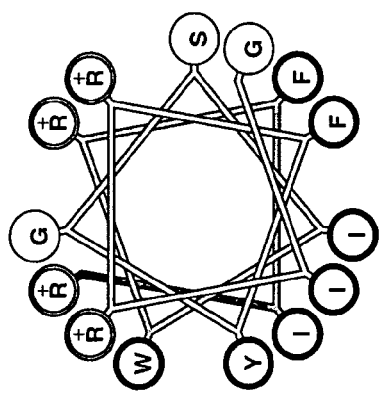
FIG. 8A is a representation of a helical wheel molecular model of R 14 L-1 peptide derived from peptide R 18L. The letters are abbreviations for amino acids. The arginines are shown to carry a positive charge.
Figure 8B:
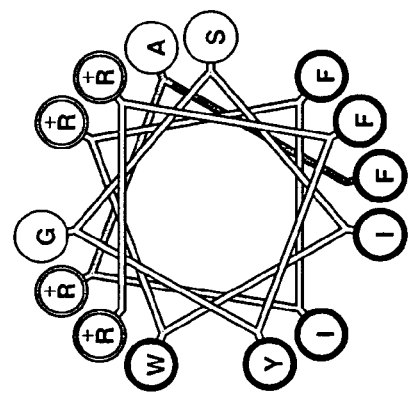
FIG. 8B is a representation of a helical wheel molecular model of R 14 L-2 peptide derived from peptide R 18L. The letters are abbreviations for amino acids. The arginines are shown to carry a positive charge. The bold circles around the letter abbreviations indicate hydrophobic residues.

Effects of Analogs of the R-18L Peptide and Effects of Different Peptide Length on Lipoprotein Uptake These experiments were performed to test shorter analogs of the peptides of the invention and their ability to facilitate and enhance lipoprotein uptake by cells. In this example, two 14-residue analogs of (R) 18L (14—residue single domain pepetides) were designed and synthesized. The (R) 18L peptide has the following sequence: Ac-(R)18L-NH$_2$: GIR-RFLGSIWRFIRAFYG (SEQ ID NO:10). One analog has the four C-terminal residues deleted and has the following sequence: Ac-(R)14L-NH$_2$ analog 1: GIRRFYGSIWRFIR (SEQ ID NO:11). Another analog has two residues each deleted from the N-terminal and the C-terminal as follows: Ac-(R)14L-NH$_2$ analog 2: —RRFYGSIWRFIRAF (SEQ ID NO:12). As shown in FIGS. 8A-8B, the R-14L-2 peptide but not the R-14-L-1 peptide enhanced the uptake of LDL in vitro. The peptide R-14L-2 but not R-14L-1 was also effective in decreasing plasma cholesterol in Apo E null mice. It is important to understand the differences between the behavior of these two peptides with respect to their secondary structure, lipid affinity and ability to associate with atherogenic lipoprotein particles. These analogs enable the determination of the mechanism by which the atherogenic lipoproteins are taken up by HepG2 cells. From these results, it was clear that positively charged Arg-containing peptides that are helical and are able to associate with atherogenic lipoproteins, are also able to enhance the uptake of atherogenic lipoproteins to result in decreased levels of plasma cholesterol. Thus, several variations of such a structure are possible.

Figure 9:
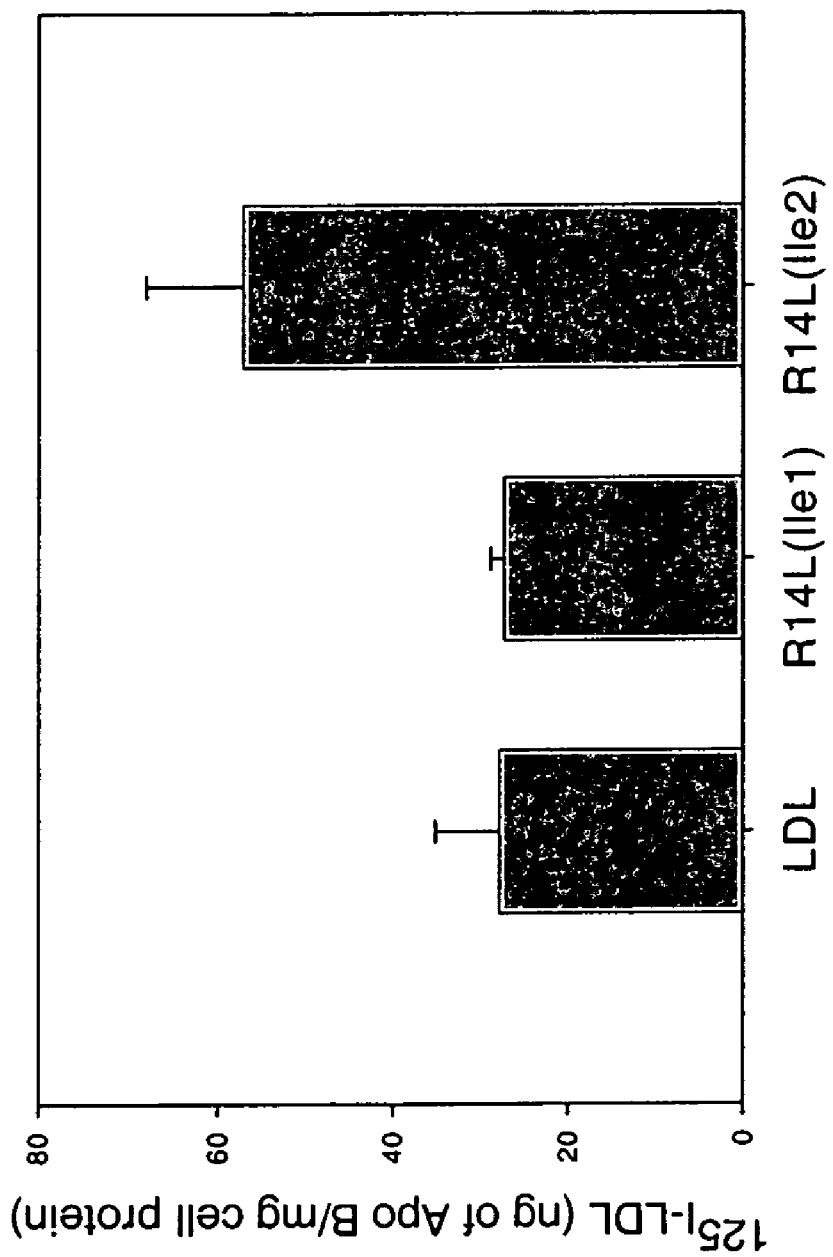
FIG. 9 is a graphic representation showing the effect of R14L peptides (R14 L containing 2 Ile residues) and R14 L (containing 1 Ile residue) on the uptake of human LDL in CHO cells measured by uptake of $^{125}$I-LDL in ng of Apo B/mg cell protein.

In FIG. 9, the effect of R14L peptides on uptake of human LDL in Chinese hamster ovary (CHO) cells is shown. CHO cells were selected because of the availability of various mutants with changes in proteoglycan expression to study the role of proteoglycans in the uptake of atherogenic lipoproteins. Similar to these in vitro results, the peptide R-14L-2 is able to enhance atherogenic lipoprotein uptake and degradation in apo E null mice. The R18L peptide was sparingly soluble in aqueous solvents. Analogs have been synthesized wherein Ile residues in all of these peptides have been replaced by Leu. The resulting peptide analogs have been found to possess increased solubility. These new analogs can be effective in enhancing hepatic uptake of atherogenic lipoproteins.

The Ac-(R)18L-NH$_2$ peptide was effective in reducing plasma cholesterol in several dyslipidemic mouse models in a dose-dependent manner. The 14-residue analogs were designed to further determine minimal structural motifs required for this reduction in plasma cholesterol, and to improve solubility at a neutral pH.

Figure 10:
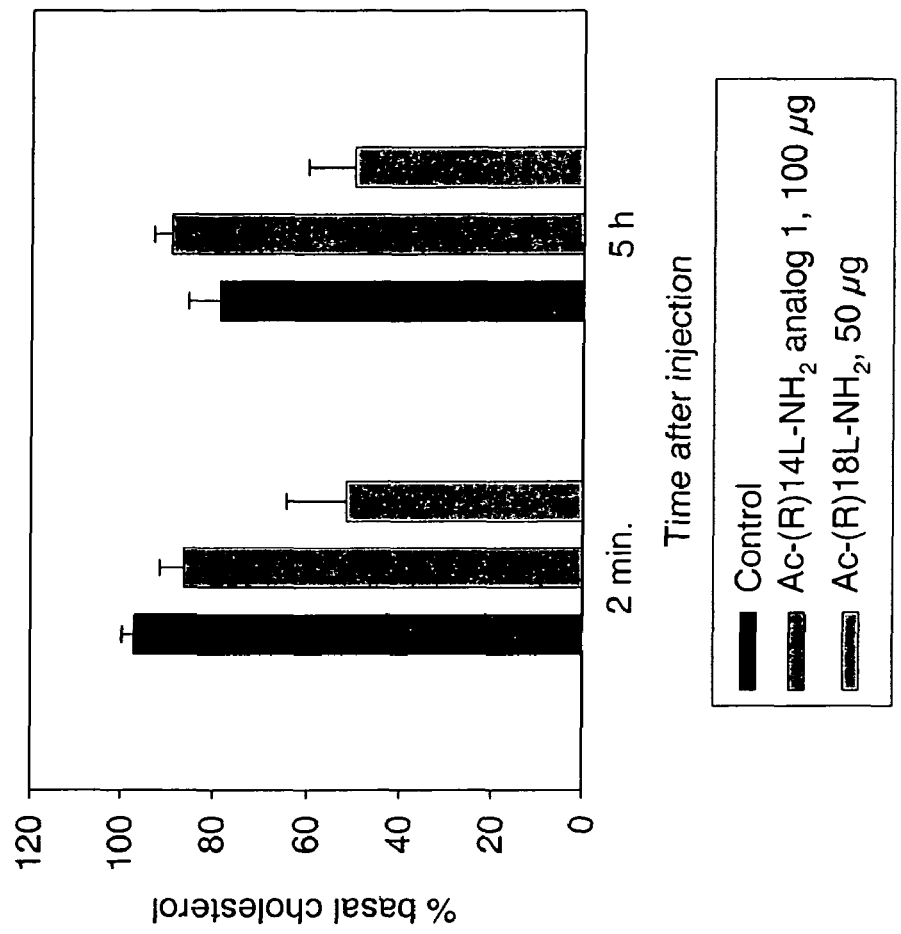
FIG. 10 is a graphic representation showing basal cholesterol levels of apo E null mice injected with two different single domain cationic peptides (Ac-(R)14L-NH$_2$ and Ac-(R)18L-NH$_2$) two (2) minutes and five (5) hours after the time of injection.

FIG. 10 shows the effects on cholesterol levels of peptides Ac-(R)14L-NH$_2$ analog 1, which is a peptide derived from the original sequence (in this case R18L) by the deletion of a part of the original sequence or substitution of existing amino acids with others or derivatizing certain functional amino acids in the sequence such as dimethylation of Lys residues, (at 100 μg/mouse; n=5) and Ac-(R)18L-NH$_2$ (at 50 μg/mouse; n=5), administered intravenously into fasted apo E null mice. The peptides were dissolved in PBS pH=5.0. Control mice (n=5) received PBS pH=5.0. Data shown represent mean±SEM.

As shown in FIG. 10, peptide Ac-(R)14L-NH$_2$ analog 1 was not effective in reducing plasma cholesterol in fasting apo E null mice when injected as free peptide at a dose of 100 μg/mouse at pH=5. Peptide Ac-(R)18L-NH$_2$ was effective in reducing plasma cholesterol in these animals at a dose of 50 μg/mouse. Peptide Ac-(R)14L-NH$_2$ analog 2 was freely soluble at pH=5.0, but at pH=7.4 was only partially soluble, with a light suspension apparent. Addition of DMPC at a 1:1 ratio (w/w) completely clarified this suspension.

Figure 11:
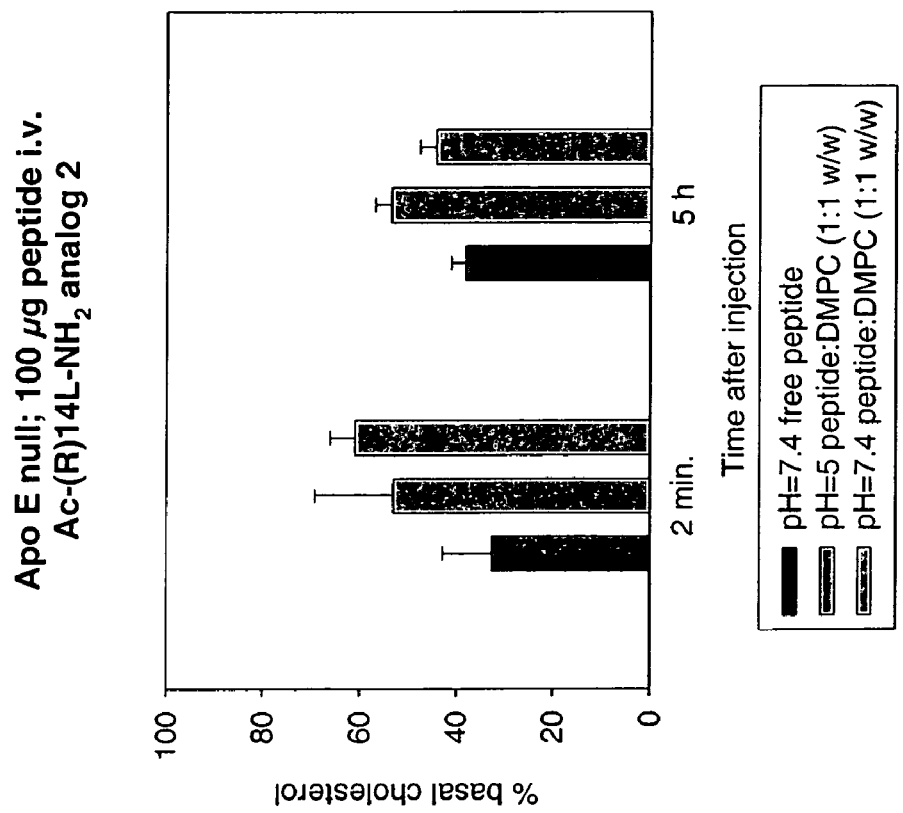
FIG. 11 is a graphic representation showing basal cholesterol levels of apo E null mice injected with Ac-(R)14L-NH$_2$ two (2) minutes or five (5) hours after injection with free peptide Ac-(R)14L-NH$_2$ at pH 7.4, with peptide:DMPC complex at pH 5.0 (1:1 w/w) or with peptide:DMPC complex at pH 7.4 (1:1 w/w).
Figure 12A:
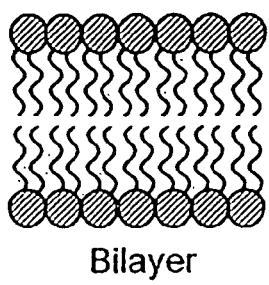
FIGS. 12A-12F are graphical illustrations of detergent micelles, membrane bilayers and inverted bilayers.
Figure 12B:
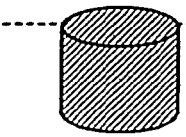
Figure 12C:
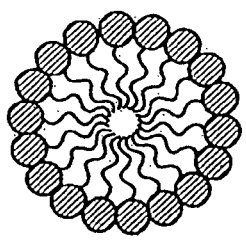
Figure 12D:
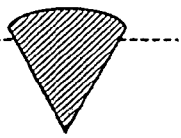
Figure 12E:
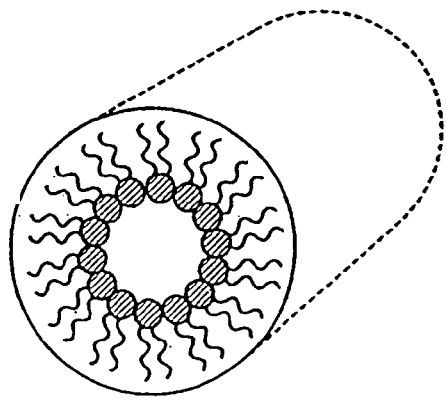
Figure 12F:

Effects on cholesterol levels of peptide Ac-(R)14L-NH$_2$ analog 2 (at 100 μg/mouse), administered intravenously into fasted apo E null mice as free peptide or as peptide:DMPC complexes at two pH levels. n=5 in all cases is shown in FIG. 11. Peptides were dissolved in PBS at the pH shown. Data shown represent mean±SEM. As shown in FIG. 11, injection of the free peptide at pH=7.4 reduced plasma cholesterol in fasting apo E null mice (100 μg/mouse, i.v.) to a greater extent than did injection of peptide:DMPC complexes at either pH=5.0 or 7.4. Peptide:DMPC complexes at either pH were essentially equivalent in their ability to reduce plasma cholesterol. These results indicate that peptide:lipid complexes are also able to enhance the uptake of atherogenic lipoproteins.

Example 4

Figures 3A, 3B:
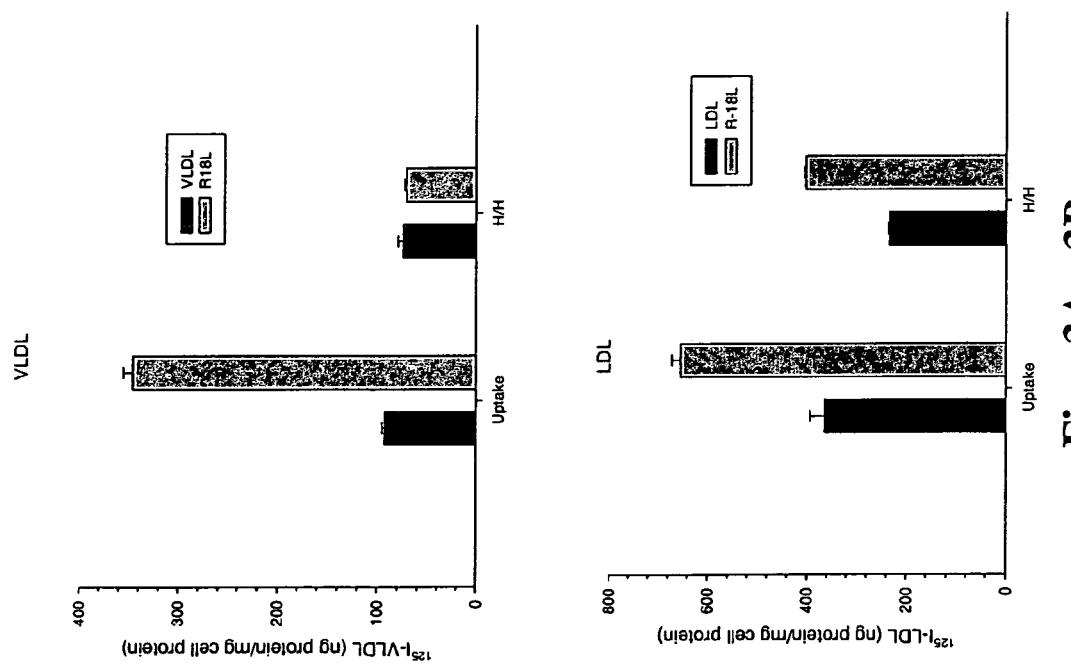
FIG. 3A is a graphic representation showing the uptake by HepG2 cells of $^{125}$I-labelled VLDL in the presence of R-18L.
FIG. 3B is a graphic representation showing the uptake by HepG2 cells of $^{125}$I-labelled VLDL in the presence of R-18L.

In vitro Assays Show R-18L Peptide Enhances Uptake of LDL and VLDL by HepG2 Cells These experiments were performed to test the bioactivity of the R-18L peptide in cell culture. In vitro studies showed that R-18L was effective in enhancing the uptake of LDL and VLDL by HepG2 cells (FIGS. 3A-3B). Specifically, $^{125}$I-LDL and $^{125}$I-VLDL and the R-18L peptide were incubated with HepG2 cells in vitro for 2 hours to determine the cellular uptake of the iodinated compounds. The cell-associated counts representing LDL and VLDL showed the uptake of LDL and VLDL by the cells. H/H represent uptake of the lipoproteins in cells treated with heparinase/heparitinase. While in the case of VLDL, the enhanced uptake was completely abrogated in the presence of H/H, there was a significant enhancement of uptake in the case of LDL. These results suggest that LDL is taken up by more than one pathway in the presence of these peptides. In case of VLDL, the peptide-mediated uptake appeared to be predominantly via an HSPG pathway. A peptide of the invention containing all-arginine residues in place of arginine and lysine residues has been shown to be the most active in HepG2 cells in enhancing the uptake and degradation of atherogenic lipoproteins. Examples of atherogenic lipoproteins are VLDL and LDL.

These studies show that the receptor binding domain, LRKL-RKRLLR (SEQ ID NO:6) (141-150 residues from Apo E) of Apo E enhances the uptake of atherogenic lipoproteins.

Example 5

Figure 5:
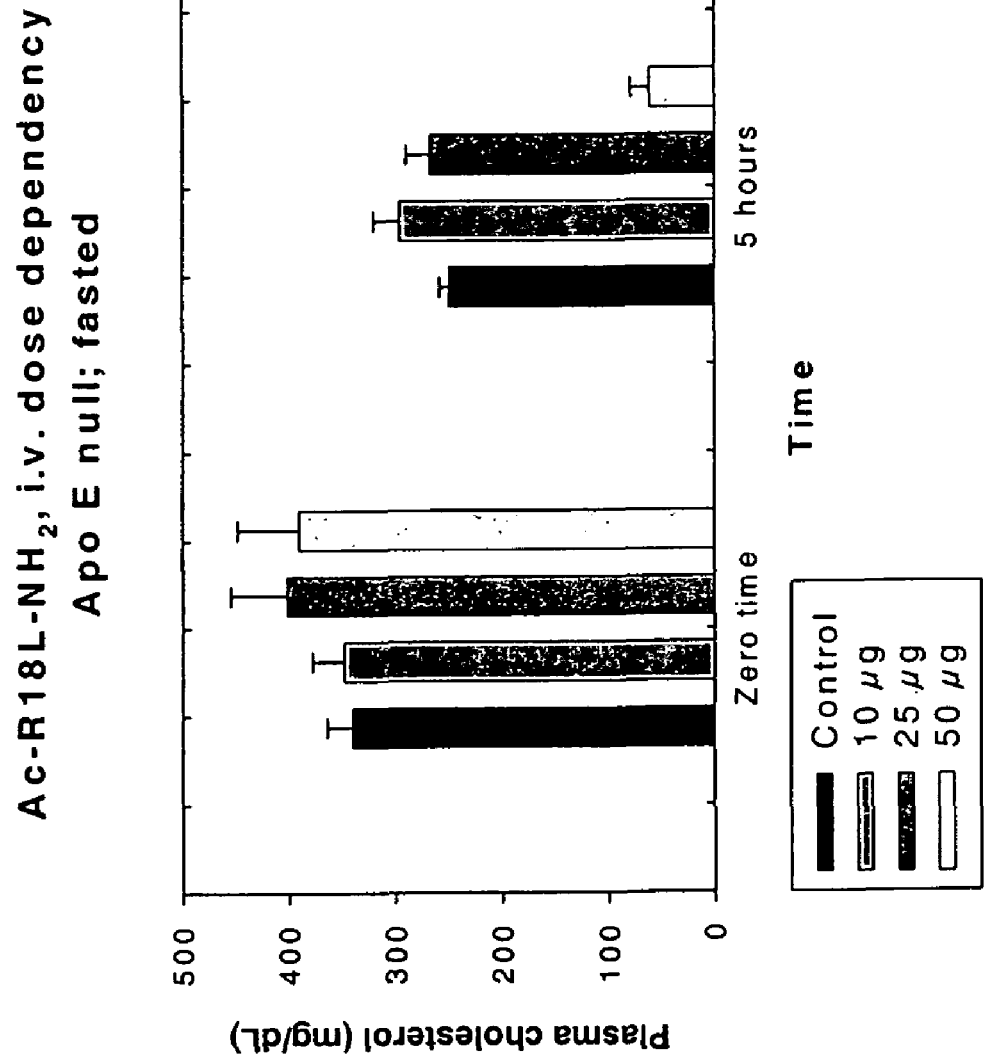
FIG. 5 is a graphic representation showing dose dependency of cholesterol reduction in blood samples from apo E null mice taken at zero (0) and five (5) hours after intravenous injection with peptide Ac-(R)18 L-NH$_2$ at 10 μg, 25 μg or 50 μg doses. The data are expressed as mean±SEM.
Figure 6:
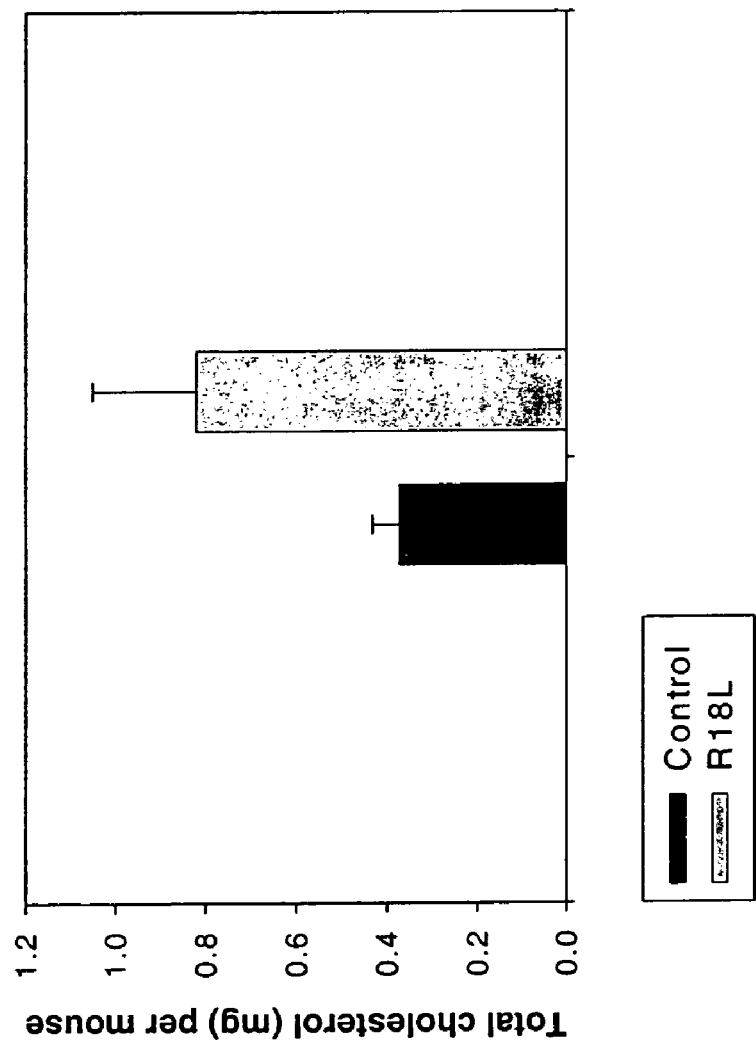
FIG. 6 is a graphic representation showing the mg of total fecal cholesterol in R18L peptide-injected animals versus control animals.

In vivo Studies Show Single Domain R-18L Peptide Lowers Plasma Cholesterol In Apo E(−) Mice More Effectively Than a Dual Domain Peptide These studies were carried out to assess the bioactivity of the single domain R-18L peptides in vivo and compare its activity with the known activity of a dual domain Apo-E derived peptide. In this case, the bioactivity refers to the activity of lowering serum cholesterol in a subject (e.g., in a transgenic mouse). In this example, the 18L peptide analogs were administered to dyslipidemic mice. Two mouse models were selected: the first was C57BL6 mice on high fat diet and the second was apo E(−) mice, which possess severe dyslipidemia (400 mg/dl to 600 mg/dl plasma cholesterol and develop atherosclerosis spontaneously even on a normal chow diet). While the peptide 18L was highly toxic to mice (four out of six mice injected with 18L 100 μg/mouse died), the R-18L single domain peptide was able to lower plasma cholesterol in apo E(−) mice more effectively than the dual domain peptide (FIGS. 5 and 6). The mice administered with R18L (100 μg/mouse) were completely normal, even when 10 times excess of 18L (lethal dosage) peptide was administered intravenously.

Using mutant cells lacking proteoglycans, results show that heparan sulphate proteoglycans (HSPG) and other receptors play a role in the uptake of dual-domain peptide-VLDL complexes. Peptide Ac-(R)18L-NH$_2$ was found to have poor solubility at neutral pH and addition of DMPC did not improve this solubility. However, Ac-(R)18L-NH$_2$:DMPC (1:1 w/w) complexes were found to be very soluble in PBS at pH=5. Thus, all experiments used PBS at pH=5 as controls.

Figure 4:
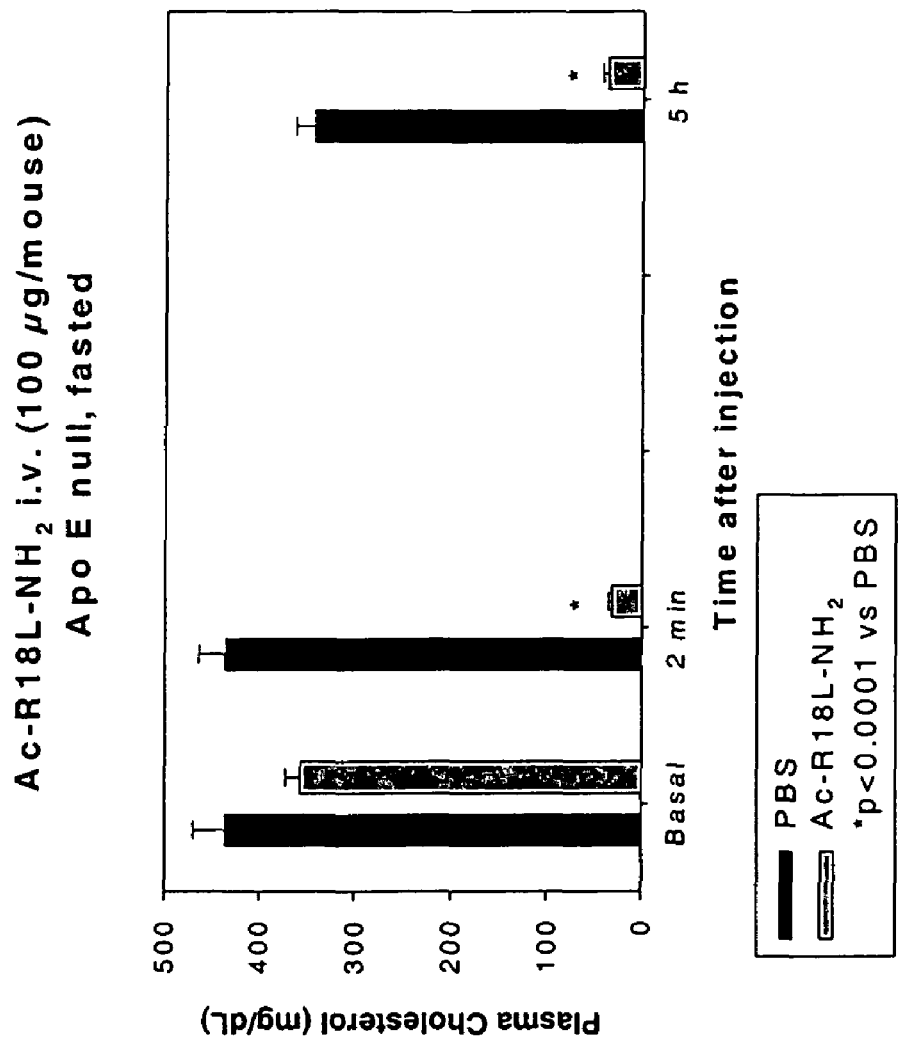
FIG. 4 is a graphic representation showing reduction of plasma cholesterol in blood samples from fasted apo E null mice after injection with peptide Ac-(R)18L-NH$_2$ compared with plasma cholesterol levels taken immediately before injection (basal levels) with the peptide. Plasma cholesterol levels were measured at 2 min after injection and 5 hours after injection. Control apo E null animals were injected with PBS.

FIG. 4 shows the level of plasma cholesterol 2 min and 5 hours after injection of apo E null mice with peptide Ac-R18L-NH$_2$ intravenously at a dose of 100 μg/mouse. Blood samples were taken immediately before injection and at 2 minutes and at 5 hours after injection and measured for cholesterol. A control of only PBS was also measured. Total cholesterol in the blood samples was measured, and is expressed in FIG. 4 as mean±SEM. When the peptide was injected into apo E null mice, plasma cholesterol was reduced by approximately 90% within two minutes and that reduction was maintained for at least five hours (FIG. 4). However, the reduction in plasma cholesterol was in the lipoproteins, including HDL. Dose dependency of cholesterol reduction in apo E null mice showed that a substantial reduction occurred at a dose of 50 μg of peptide per mouse (FIG. 5), and that reduction was limited to the VLDL and IDL/LDL fractions. FIG. 5 shows dose dependency of cholesterol reduction in apo E null mice and shows reduction at the dose of 50 μg/mouse. Feces were collected for 24 hours following injection of 100 μg of Ac-(R)18L-NH$_2$:DMPC complexes (n=2) or PBS (n=5). Fecal sterols were extracted, and total cholesterol was determined manually (Sigma Infinity). As shown in FIG. 6, total fecal cholesterol from peptide-injected animals was nearly twice that of PBS-injected controls, suggesting increased hepatic secretion of cholesterol (and, presumably, bile salts) into the gut. Total feces were collected from individually-caged mice for 24 hours following intravenous injection of Ac-(R)18L-NH$_2$ into apo E null mice at a dose of 100 μg/mouse. Total 24-hour fecal cholesterol was then calculated. Feces from each mouse were weighed, lyophilized, and then re-weighed. 100 mg dried feces was then homogenized, and total lipids were extracted. The dried extract was resuspended in isopropanol, and cholesterol was measured manually. Data shown in FIG. 6 are mean±SEM for control and mean±range for peptide.

Figure 7:
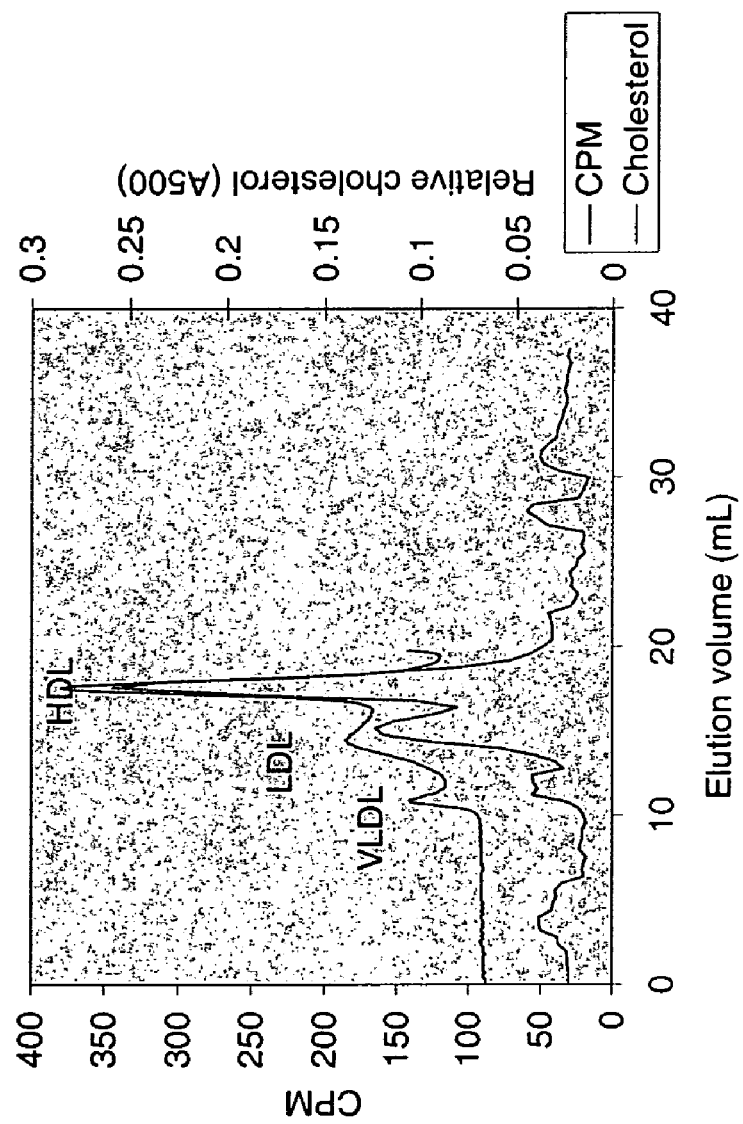
FIG. 7 is a graphic representation showing the plasma lipoprotein profile from an in vivo mixing experiment. The relative cholesterol eluting shows three peaks: VLDL, LDL and HDL at elution volume (mL) c. 12, 16 and 18. The counts per minute (CPM) detected show peaks at similar intensity and at the same elution volume as the cholesterol. VLDL shows a CPM of c. 50, LDL shows a CPM of c. 150 and HDL shows a CPM of c. 350.

In contrast to Ac-hE18A-NH$_2$, [$^{125}$I]Ac-(R)18L-NH$_2$:DMPC complexes were able to associate with LDL from LDL-R null mice (FIG. 7). Peptide [$^{125}$I]Ac-(R)18L-NH$_2$ was mixed with plasma from an LDL-R null mouse at a proportion of 100 µg peptide:1 mL plasma. The plasma lipoprotein profile was determined using the CLiP method (Garber and Anantharamaiah, *J. Lipid. Res.*, 2000), and fractions were collected for measurement of radioactivity. Thus, peptide:lipid complexes are good candidates for administration that would result in enhanced uptake of atherogenic lipoproteins. The effect of the single domain peptide of the invention should last longer than any dual domain peptide since lipid-associated peptide is helical and the backbone is not accessible for proteolytic cleavage (degradation). Thus, several slow-release formulations of peptides with lipids are tested to determine the optimal formulation for delivery.

Since binding of the peptide of the invention to a lipoprotein surface is the main requirement for the enhanced uptake of atherogenic lipoproteins, shorter peptides derived from 18L were designed, synthesized and tested. For this purpose, two peptides were derived from R-18L. This is shown in FIG. 8A (peptide R14 L-1) and FIG. 8B (peptide R14-L2). In the linear sequence of R-18L:GIRRFLGSIWRFIRAFVG (SEQ ID NO:4) two amino acids on the N- and C-termini are removed (R-14L-1, FIG. 8A) and four amino acids from N-terminus of R18L are deleted (in R-14L-2, FIG. 8B). Shortening of the peptide may have an effect on the secondary structure and lipid affinity. However, a Y and a W were maintained in both the analogs to enable fluorescence studies and radiolabeling of the peptide analogs.

Example 6

Making Compositions and Formulations of the Polypeptide of the Invention

A. Synthesis of Peptides of the Invention

Peptide synthesis is a routine method that would be well known by one of ordinary skill in the art. There are service companies that exist which provide the service of making peptides given a desired amino acid sequence. In a non-limiting example, peptides are synthesized by the solid phase method using automatic peptide synthesizer using the Fmoc chemistry. Typically, rink amide resin is used for the synthesis. Fmoc amino acids are added using HBTU and FMOC at each stage of the synthesis and is removed by treating the blocked products with piperidine. After the addition of amino acids, the N-terminal amino group is acetylated using acetic anhydride. The peptide resin is treated with 70% triflouroacetic acid in dichloromethane (in presence of 1% anisole, 1% metcaptoethanol and 1% water). After the evaporation of the solvent, ether is added and the precipitate washed with additional amounts of ether. The peptide is purified by using HPLC (C-4 Michell Muller column) 35-60% acetonitrile (in the presence of 0.1% trifluoroacetic acid) in 5 hrs with a flow rate of 4 ml/min. The purity of the peptide was determined by analytical HPLC and mass spectral analyses.

B. Preparation of Peptide Lipid Complexes

The peptide of the invention easily associates with dimyristoylphosphatidyl choline (DMPC), egg PC, palmitoyloleylphosphatidyl choline (POPC). Peptide and lipid mixtures (1:5 by weight ratio) are prepared by spontaneous mixing. A clear solution is obtained upon mixing of peptide with lipid. Whether the peptide:lipid complex is clear or not, the mixture is sterilized by membrane filtration and used for experiments.

C. Peptide:Lipid Slow Release Formulations

The following description provides how to make peptide:lipid slow release formulations. The slow release lipid formulations of peptide using lipid mixtures can be prepared using the following general procedure (Ramprasad, M. P. et al., *J. Controlled Release* 79:207-218, 2002). Specifically, in a non-limiting example, 6 ml of an aqueous solution of the peptide (2 mg/ml containing 25 mM acetic acid, pH 4.0 and 4% sucrose) is emulsified with 6 ml of chloroform solution containing phospholipids (13.2 mM dipalmitoylphosphatidyl choline (DPPC), 13.2 mM dioleylphosphatidyl choline (DOPC) and 5.6 mM dipalmitoylphosphatidyl glycerol (DPPG) cholesterol (39.8 mM), and triglycerides (2.44 mM triolin and 2.44 mM tricaprylin). This first emulsion is mixed with the second aqueous solution containing 3.2% glucose and 40 mM lysine to form the water-in-oil-water (second) emulsion. Chloroform is removed by flushing nitrogen over the surface of the mixture at 37° C. The resulting emulsion MLV particles are harvested by centrifugation for 10 min at 600×g, washed, and resuspended in isotonic buffer. Such a procedure has been used for the dual-domain peptide slow release when administered in dyslipidemic mice (Id.).

Example 7

Binding, Internalization and Degradation of Atherogenic Lipoproteins in Cultured Cells This experiment was carried out to follow the events subsequent to the binding of atherogenic lipoproteins to cultured cells. HepG2 cells (obtained from American Type Culture Collection (ATCC), Manassas, Va.) are used for determining peptide-mediated enhanced uptake of LDL or VLDL. Cells are grown in DMEM in six-well plates and used at 75% to 90% confluence. The seeding density of the cells that is used is 1.5-3.0×10$^5$ cells/ml. Cells are treated with DMEM containing lipoprotein-deficient serum (LPDS) 24 h prior to use to upregulate LDL incubated with the indicated concentration (0 to 50 µg of $^{125}$I-LDL) at 4° C. for 2 h in presence or absence of peptides. Nonspecific binding is assessed in the presence of 50-fold excess of unlabelled LDL with or without peptides. After washing with ice-cold PBS, (containing 2 mg/ml BSA) to remove excess labeled lipoproteins, cells are incubated with excess dextran sulfate (4 mg/ml Pharmacia, M$_r$ of 500,000) or heparin (Sigma Chemical Co., St. Louis, Mo., 10 mg/ml) for 1 h to release specifically bound $^{125}$I-LDL. The counts in the dextran sulfate wash reflect the amount of LDL bound to cells. Cells are then washed with PBS and then dissolved in 0.1 N NaOH and a 0.5 ml aliquot of the cells suspension is counted. The counts reflect the amount of LDL internalized. The amount of protein is estimated using the Lowry method. Degradation of LDL is assessed by precipitating $^{125}$I-LDL using 17% trifluoroacetic acid and incubating at 4° C. for 30 min. The precipitate is removed by centrifugation. The supernatant is treated with 10 µl of 40% KI and 40 µl of 10% hydrogen peroxide. The free $^{125}$I is extracted with 2 ml chloroform. The upper aqueous layer is then counted for radioactivity. These counts represent the amount of monoiodi-tyrosine produced by the degradation of apo B in lipoproteins. Cell surface HSPG is removed by treating cells with heparinase and heparitinase (Sigma Chemical Co., St. Louis, Mo.) at a concentration of 3 u/ml of medium for 2 h at 37° C. In all cell experiments an average value of triplicate experiments are considered. Counts are detected inside the cultured cells and it is shown that LDL and VLDL are bound, internalized and degraded in the cultured cells in the presence of the peptide of the invention.

Example 8

In vivo Studies

This experiment is carried out to show the usefulness of the peptides of the invention in vivo for lowering serum cholesterol. Peptide or peptide-lipid complexes were administered intravenously to mice. After some time period (as specifically shown in various figures), plasma samples were obtained by performing a retro-orbital bleed of the animals. The samples were analyzed by the column lipoprotein profile as previously described (Garber, D. et al. *J. Lipid Res.* 2000, 41:1020-1026). Briefly, 5 to 10 μl of the plasma was analyzed using a single superose (Pharmacia, Piscataway, N.J.) column. Immediately following the column run, cholesterol reagent is introduced through a mixing tee, and the eluent:reagent mixture enters a post column reaction coil. Cholesterol content of the reaction mixture is determined at 500 nm spectrophotometrically and the data points are collected into a computer. The resulting profiles are decomposed into component peaks and analyzed for relative area using PeakFit® computer software (SPSS Science, Chicago, Ill.). Absolute cholesterol value for total cholesterol is determined by comparisons with control samples of known values. The results would show a decrease in serum cholesterol in the subjects that received the polypeptides of the invention.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A synthetic apolipoprotein-E mimicking polypeptide comprising an amino acid sequence selected from the group of
   (i) Arg-Arg-Phe-Tyr-Gly-Ser-Ile-Trp-Arg-Phe-Ile Arg-Ala-Phe (SEQ ID NO: 12) or the reverse sequence thereof,
   (ii) Arg-Arg-Phe-Tyr-Gly-Ser-Leu-Trp-Arg-Phe-Leu-Arg-Ala-Phe (SEQ ID NO: 139) or the reverse sequence thereof, and
   (iii) Arg-Arg-Phe-Tyr-Gly-Ser-Ile-Trp-Arg-Phe-Leu-Arg-Ala-Phe (SEQ ID NO: 143) or the reverse sequence thereof, wherein the polypeptide comprises an acetyl group at the N-terminus and an amide group at the C-terminus, and wherein the polypeptide is capable of forming an amphipathic α helical structure.

2. The polypeptide of claim 1, wherein the polypeptide comprises at least 14 amino acids in length.

3. The polypeptide of claim 1, which is a recombinant polypeptide.

4. The polypeptide of claim 1, which is a peptidomimetic.

5. The polypeptide of claim 1, wherein the polypeptide enhances binding of low-density lipoprotein (LDL) or very low density lipoprotein (VLDL) to a cell.

6. The polypeptide of claim 1, wherein the polypeptide enhances degradation of low-density lipoprotein (LDL) or very low density lipoprotein (VLDL) by a cell.

7. A composition comprising the polypeptide of claim 1 and a pharmaceutically acceptable carrier.

8. The composition of claim 7, wherein the carrier comprises dimyristoylphosphatidyl (DMPC), phosphate buffered saline or a multivesicular liposome.

9. An isolated nucleic acid encoding the polypeptide of claim 1.

10. The nucleic acid of claim 9, wherein the nucleic acid comprises DNA, RNA or cDNA.

11. A vector comprising the nucleic acid of claim 9.

12. An isolated host cell comprising the nucleic acid of claim 9.

13. The isolated host cell of claim 12, which is eukaryotic or prokaryotic.

14. An isolated recombinant cell comprising the nucleic acid of claim 9.

15. An isolated recombinant cell producing the polypeptide of claim 1.

16. A method for enhancing LDL binding to a hepatic cell, the method comprising contacting the cell with the polypeptide of claim 1.

17. A method for enhancing LDL and VLDL binding to a hepatic cell in a subject, the method comprising administering a composition comprising the polypeptide of claim 1 to the subject in an amount effective to increase LDL and VLDL binding to the cell of the subject.

18. The method of claim 17, wherein the administration is oral, parenteral, by intramuscular injection, by intraperitoneal injection, or transdermal.

19. The method of claim 17, wherein the subject is a human subject.

20. The method of claim 17, wherein the subject is a mouse, a rat, a rabbit, a cow, a sheep, a pig, or a primate.

21. The method of claim 20, wherein the primate is a human, a monkey, an ape, a chimpanzee, or an orangutan.

22. A method for reducing serum cholesterol level in a subject, the method comprising the step of administering to the subject a composition comprising the polypeptide of claim 1 in an amount effective to increase binding of LDL and/or VLDL to hepatic cells in the subject, thereby reducing serum cholesterol level in the subject.

23. A method for treating a subject with coronary artery disease, the method comprising the step of administering to the subject a composition comprising an effective amount of the polypeptide of claim 1, to thereby treat the subject.

24. A method for treating a subject with dysbetalipoproteinemia, the method comprising the step of administering to the subject a composition comprising an effective amount of the polypeptide of claim 1, to thereby treat the subject.

25. A method for reducing the risk of myocardial infarction in a subject, the method comprising the step of administering to the subject a composition comprising an effective amount of the polypeptide of claim 1, to thereby treat the subject.

26. A method for treating atherosclerosis in a subject, the method comprising the step of administering to the subject a composition comprising an effective amount of the polypeptide of claim 1, to thereby treat the subject.

* * * * *

SEQUENCE LISTING

```
<160> NUMBER OF SEQ ID NOS: 210

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 1

Gly Ile Lys Lys Phe Leu Gly Ser Ile Trp Lys Phe Ile Trp Lys Phe
 1               5                  10                  15

Ile Lys Ala Tyr Gly
            20

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 2

Gly Ile Arg Arg Phe Leu Gly Ser Ile Trp Arg Phe Ile Arg Ala Phe
 1               5                  10                  15

Tyr Gly

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 3

Asp Trp Leu Lys Ala Phe Tyr Asp Lys Val Ala Glu Lys Leu Lys Glu
```

```
                1               5                  10                  15
Ala Phe

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ile Arg Arg Phe Leu Gly Ser Ile Trp Arg Phe Ile Arg Ala Phe
  1               5                  10                  15

Val Gly

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ile Arg Arg Phe Leu Gly Ser Ile Trp Arg Phe Ile Arg Ala Phe
  1               5                  10                  15

Tyr Gly

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Arg Lys Leu Arg Lys Arg Leu Leu Arg
  1               5                  10

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ile Lys Lys Phe Leu Gly Ser Ile Trp Lys Phe Ile Lys Ala Phe
  1               5                  10                  15

Val Gly

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ile Arg Arg Phe Leu Gly Ser Ile Trp Arg Phe Ile Arg Ala Phe
  1               5                  10                  15
```

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Asp Trp Leu Lys Ala Phe Tyr Asp Lys Val Ala Glu Lys Leu Ala Glu
1               5                   10                  15

Ala Phe

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Gly Ile Arg Arg Phe Leu Gly Ser Ile Trp Arg Phe Ile Arg Ala Phe
1               5                   10                  15

Tyr Gly

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gly Ile Arg Arg Phe Tyr Gly Ser Ile Trp Arg Phe Ile Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Arg Arg Phe Tyr Gly Ser Ile Trp Arg Phe Ile Arg Ala Phe
1               5                   10

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Gly Ile Arg Arg Phe Leu Gly Ser Ile Trp Arg Phe Ile Arg Ala Phe
1               5                   10                  15

Tyr Gly

<210> SEQ ID NO 14

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ile Trp Arg Phe Leu Gly Ser Ile Arg Arg Phe Ile Arg Ala Phe
 1               5                  10                  15

Tyr Gly

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ile Gly Arg Phe Leu Arg Ser Ile Trp Gly Phe Ile Arg Ala Phe
 1               5                  10                  15

Tyr Arg

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ile Arg Arg Phe Leu Gly Ser Ile Trp Arg Phe Ile Gly Ala Phe
 1               5                  10                  15

Tyr Arg

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ile Arg Arg Phe Leu Gly Ser Ile Trp Ala Phe Ile Arg Arg Phe
 1               5                  10                  15

Tyr Gly

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ile Arg Arg Phe Leu Ser Gly Ile Trp Arg Phe Ile Arg Ala Phe
 1               5                  10                  15

Tyr Gly

<210> SEQ ID NO 19
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ile Arg Arg Phe Leu Ser Gly Ile Trp Ala Phe Ile Arg Ala Phe
 1               5                  10                  15

Tyr Gly

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ile Trp Arg Phe Leu Ser Gly Ile Arg Arg Phe Ile Arg Ala Phe
 1               5                  10                  15

Tyr Gly

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ile Arg Arg Phe Leu Gly Ala Ile Trp Arg Phe Ile Arg Ser Phe
 1               5                  10                  15

Tyr Gly

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ile Trp Arg Phe Leu Gly Ala Ile Trp Arg Phe Ile Arg Ser Phe
 1               5                  10                  15

Tyr Gly

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr Phe Ala Arg Ile Phe Arg Trp Ile Ser Gly Leu Phe Arg Arg
 1               5                  10                  15

Ile Gly

<210> SEQ ID NO 24
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Tyr Phe Ala Arg Ile Phe Arg Arg Ile Ser Gly Leu Phe Arg Trp
 1               5                  10                  15

Ile Gly

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Tyr Phe Ala Arg Ile Phe Gly Trp Ile Ser Arg Leu Phe Arg Gly
 1               5                  10                  15

Ile Gly

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Tyr Phe Ala Gly Ile Phe Arg Trp Ile Ser Arg Leu Phe Arg Gly
 1               5                  10                  15

Ile Gly

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Tyr Phe Arg Arg Ile Phe Ala Trp Ile Ser Gly Leu Phe Arg Arg
 1               5                  10                  15

Ile Gly

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Phe Ala Arg Ile Phe Arg Trp Ile Gly Ser Leu Phe Arg Arg
 1               5                  10                  15

Ile Gly

<210> SEQ ID NO 29
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Tyr Phe Ala Arg Ile Phe Arg Trp Ile Gly Ser Leu Phe Arg Arg
  1               5                  10                  15

Ile Gly

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Tyr Phe Arg Arg Ile Phe Arg Arg Ile Gly Ser Leu Phe Ala Trp
  1               5                  10                  15

Ile Gly

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Tyr Phe Ser Arg Ile Phe Arg Trp Ile Ala Gly Leu Phe Arg Arg
  1               5                  10                  15

Ile Gly

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Tyr Phe Ser Arg Ile Phe Arg Trp Ile Ala Gly Leu Phe Arg Trp
  1               5                  10                  15

Ile Gly

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: (DiMe)Lys
<220> FEATURE:
<221> NAME/KEY: MOD_RES
<222> LOCATION: (10)
<223> OTHER INFORMATION: (DiMe)Lys
<220> FEATURE:
<221> NAME/KEY: MOD_RES
```

```
<222> LOCATION: (15)
<223> OTHER INFORMATION: (DiMe)Lys

<400> SEQUENCE: 33

Gly Ile Lys Lys Phe Leu Gly Trp Ile Lys Ala Phe Ile Ser Lys Phe
 1               5                  10                  15

Tyr Gly

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (10)..(11)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 34

Gly Ile Trp Lys Phe Leu Gly Ser Ile Lys Lys Phe Ile Lys Ala Phe
 1               5                  10                  15

Tyr Gly

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (7)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys
<220> FEATURE:
<221> NAME/KEY: MOD_RES
<222> LOCATION: (18)
<223> OTHER INFORMATION: (DiMe)Lys

<400> SEQUENCE: 35

Gly Ile Gly Lys Phe Leu Lys Ser Ile Trp Gly Phe Ile Lys Ala Phe
 1               5                  10                  15

Tyr Lys

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (3)..(4)
<223> OTHER INFORMATION: (DiMe)Lys
<220> FEATURE:
<221> NAME/KEY: MOD_RES
<222> LOCATION: (11)
<223> OTHER INFORMATION: (DiMe)Lys
<220> FEATURE:
<221> NAME/KEY: MOD_RES
<222> LOCATION: (18)
<223> OTHER INFORMATION: (DiMe)Lys

<400> SEQUENCE: 36

Gly Ile Lys Lys Phe Leu Gly Ser Ile Trp Lys Phe Ile Gly Ala Phe
 1               5                  10                  15

Tyr Lys

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: (DiMe)Lys
<220> FEATURE:
<221> NAME/KEY: MOD_RES
<222> LOCATION: (14)..(15)
<223> OTHER INFORMATION: (DiMe)Lys

<400> SEQUENCE: 37

Gly Ile Lys Lys Phe Leu Gly Ser Ile Trp Ala Phe Ile Lys Lys Phe
 1               5                  10                  15

Tyr Gly

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: (DiMe)Lys
<220> FEATURE:
<221> NAME/KEY: MOD_RES
<222> LOCATION: (11)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 38

Gly Ile Lys Lys Phe Leu Ser Gly Ile Trp Lys Phe Ile Lys Ala Phe
 1               5                  10                  15

Tyr Gly

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (3)..(4)
<223> OTHER INFORMATION: (DiMe)Lys
<220> FEATURE:
<221> NAME/KEY: MOD_RES
<222> LOCATION: (14)..(15)
<223> OTHER INFORMATION: (DiMe)Lys

<400> SEQUENCE: 39

Gly Ile Lys Lys Phe Leu Ser Gly Ile Trp Phe Ile Ala Lys Lys Phe
 1               5                  10                  15

Tyr Gly

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (10)..(11)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 40

Gly Ile Trp Lys Phe Leu Ser Gly Ile Lys Lys Phe Ile Lys Ala Phe
 1               5                  10                  15

Tyr Gly

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: (DiMe)Lys
<220> FEATURE:
<221> NAME/KEY: MOD_RES
<222> LOCATION: (11)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 41

Gly Ile Lys Lys Phe Leu Gly Ala Ile Trp Lys Phe Ile Lys Ser Phe
 1               5                  10                  15

Tyr Gly

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)
<223> OTHER INFORMATION: (DiMe)Lys
<220> FEATURE:
<221> NAME/KEY: MOD_RES
<222> LOCATION: (10)..(11)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 42

Gly Ile Trp Lys Phe Leu Gly Ala Ile Lys Lys Phe Ile Lys Ser Phe
 1               5                  10                  15

Tyr Gly

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (8)
<223> OTHER INFORMATION: (DiMe)Lys
<220> FEATURE:
<221> NAME/KEY: MOD_RES
<222> LOCATION: (15)..(16)
<223> OTHER INFORMATION: (DiMe)Lys

<400> SEQUENCE: 43

Gly Tyr Phe Ala Lys Ile Phe Lys Trp Ile Ser Gly Leu Phe Lys Lys
 1               5                  10                  15

Ile Gly

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (8)..(9)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 44

Gly Tyr Phe Ala Lys Ile Phe Lys Lys Ile Ser Gly Leu Phe Lys Trp
 1               5                  10                  15

Ile Gly

<210> SEQ ID NO 45
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: (DiMe)Lys
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (12)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 45

Lys Tyr Phe Ala Lys Ile Phe Gly Trp Ile Ser Lys Leu Phe Lys Gly
 1               5                  10                  15

Ile Gly

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: (DiMe)Lys
<220> FEATURE:
<221> NAME/KEY: MOD_RES
<222> LOCATION: (8)
<223> OTHER INFORMATION: (DiMe)Lys
<220> FEATURE:
<221> NAME/KEY: MOD_RES
<222> LOCATION: (12)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 46

Lys Tyr Phe Ala Gly Ile Phe Lys Trp Ile Ser Lys Leu Phe Lys Gly
 1               5                  10                  15

Ile Gly

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: (DiMe)Lys
<220> FEATURE:
<221> NAME/KEY: MOD_RES
<222> LOCATION: (15)..(16)
<223> OTHER INFORMATION: (DiMe)Lys

<400> SEQUENCE: 47

Gly Tyr Phe Lys Lys Ile Phe Ala Trp Ile Ser Gly Leu Phe Lys Lys
 1               5                  10                  15
```

Ile Gly

```
<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (8)
<223> OTHER INFORMATION: (DiMe)Lys
<220> FEATURE:
<221> NAME/KEY: MOD_RES
<222> LOCATION: (15)..(16)
<223> OTHER INFORMATION: (DiMe)Lys

<400> SEQUENCE: 48

Gly Tyr Phe Ala Lys Ile Phe Lys Trp Ile Gly Ser Leu Phe Lys Lys
 1               5                  10                  15

Ile Gly
```

```
<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (8)
<223> OTHER INFORMATION: (DiMe)Lys
<220> FEATURE:
<221> NAME/KEY: MOD_RES
<222> LOCATION: (15)..(16)
<223> OTHER INFORMATION: (DiMe)Lys

<400> SEQUENCE: 49

Gly Tyr Phe Ala Lys Ile Phe Lys Trp Ile Gly Ser Leu Phe Lys Lys
 1               5                  10                  15

Ile Gly
```

```
<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: (DiMe)Lys
<220> FEATURE:
<221> NAME/KEY: MOD_RES
<222> LOCATION: (8)..(9)
<223> OTHER INFORMATION: (DiMe)Lys

<400> SEQUENCE: 50

Gly Tyr Phe Lys Lys Ile Phe Lys Lys Ile Gly Ser Leu Phe Ala Trp
 1               5                  10                  15
```

Ile Gly

```
<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (8)
<223> OTHER INFORMATION: (DiMe)Lys
<220> FEATURE:
<221> NAME/KEY: MOD_RES
<222> LOCATION: (15)..(16)
<223> OTHER INFORMATION: (DiMe)Lys

<400> SEQUENCE: 51
```

Gly Tyr Phe Ser Lys Ile Phe Lys Trp Ile Ala Gly Leu Phe Lys Lys
 1               5                  10                  15

Ile Gly

```
<210> SEQ ID NO 52
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (8)..(9)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 52
```

Gly Tyr Phe Ser Lys Ile Phe Lys Lys Ile Ala Gly Leu Phe Lys Trp
 1               5                  10                  15

Ile Gly

```
<210> SEQ ID NO 53
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 53
```

Gly Ile Lys Arg Phe Leu Gly Ser Ile Trp Arg Phe Ile Lys Ala Phe
 1               5                  10                  15

-continued

Tyr Gly

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 54

Gly Ile Trp Lys Phe Leu Gly Ser Ile Arg Arg Phe Ile Lys Ala Phe
 1               5                  10                  15

Tyr Gly

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (18)
<223> OTHER INFORMATION: (DiMe)Lys

<400> SEQUENCE: 55

Gly Ile Gly Lys Phe Leu Arg Ser Ile Trp Gly Phe Ile Arg Ala Phe
 1               5                  10                  15

Tyr Lys

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (DiMe)Lys
<220> FEATURE:
<221> NAME/KEY: MOD_RES
<222> LOCATION: (18)
<223> OTHER INFORMATION: (DiMe)Lys

<400> SEQUENCE: 56

Gly Ile Lys Arg Phe Leu Gly Ser Ile Trp Arg Phe Ile Gly Ala Phe
 1               5                  10                  15

Tyr Lys

<210> SEQ ID NO 57
<211> LENGTH: 18
<212> TYPE: PRT
<213> ORGANISM: Artificial Sequence
<220> FEATURE:

-continued

```
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 57

Gly Ile Arg Lys Phe Leu Gly Ser Ile Trp Ala Phe Ile Lys Arg Phe
  1               5                  10                  15

Tyr Gly

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 58

Gly Ile Arg Lys Phe Leu Ser Gly Ile Trp Arg Phe Ile Lys Ala Phe
  1               5                  10                  15

Tyr Gly

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 59

Gly Ile Arg Lys Phe Leu Ser Gly Ile Trp Ala Phe Ile Lys Ala Phe
  1               5                  10                  15

Tyr Gly

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
```

```
<222> LOCATION: (14)
<223> OTHER INFORMATION: (DiMe)Lys

<400> SEQUENCE: 60

Gly Ile Trp Lys Phe Leu Ser Gly Ile Arg Arg Phe Ile Lys Ala Phe
 1               5                  10                  15

Tyr Gly

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 61

Gly Ile Lys Arg Phe Leu Gly Ala Ile Trp Arg Phe Ile Lys Ser Phe
 1               5                  10                  15

Tyr Gly

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (14)
<223> OTHER INFORMATION: (DiMe)Lys

<400> SEQUENCE: 62

Gly Ile Trp Lys Phe Leu Gly Ala Ile Trp Arg Phe Ile Lys Ser Phe
 1               5                  10                  15

Tyr Gly

<210> SEQ ID NO 63
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (DiMe)Lys
<220> FEATURE:
<221> NAME/KEY: MOD_RES
<222> LOCATION: (10)
<223> OTHER INFORMATION: (DiMe)Lys

<400> SEQUENCE: 63

Gly Ile Lys Arg Phe Leu Gly Trp Ile Lys Ala Phe Ile Ser Arg Phe
 1               5                  10                  15
```

Tyr Gly

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 64

Gly Tyr Phe Ala Lys Ile Phe Arg Trp Ile Ser Gly Leu Phe Lys Arg
 1               5                  10                  15

Ile Gly

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 65

Gly Tyr Phe Ala Lys Ile Phe Arg Arg Ile Ser Gly Leu Phe Lys Trp
 1               5                  10                  15

Ile Gly

<210> SEQ ID NO 66
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 66

Arg Tyr Phe Ala Lys Ile Phe Gly Trp Ile Ser Arg Leu Phe Lys Gly
 1               5                  10                  15

Ile Gly

<210> SEQ ID NO 67
<211> LENGTH: 18
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 67

Arg Tyr Phe Ala Gly Ile Phe Lys Trp Ile Ser Arg Leu Phe Lys Gly
 1               5                  10                  15

Ile Gly

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 68

Gly Tyr Phe Arg Lys Ile Phe Ala Trp Ile Ser Gly Leu Phe Lys Arg
 1               5                  10                  15

Ile Gly

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 69

Gly Tyr Phe Ala Lys Ile Phe Arg Trp Ile Gly Ser Leu Phe Lys Arg
 1               5                  10                  15

Ile Gly

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
```

```
<222> LOCATION: (16)
<223> OTHER INFORMATION: (DiMe)Lys

<400> SEQUENCE: 70

Gly Tyr Phe Ala Lys Ile Phe Arg Trp Ile Gly Ser Leu Phe Arg Lys
 1               5                  10                  15

Ile Gly

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (DiMe)Lys
<220> FEATURE:
<221> NAME/KEY: MOD_RES
<222> LOCATION: (9)
<223> OTHER INFORMATION: (DiMe)Lys

<400> SEQUENCE: 71

Gly Tyr Phe Lys Arg Ile Phe Arg Lys Ile Gly Ser Leu Phe Ala Trp
 1               5                  10                  15

Ile Gly

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: (DiMe)Lys
<220> FEATURE:
<221> NAME/KEY: MOD_RES
<222> LOCATION: (15)
<223> OTHER INFORMATION: (DiMe)Lys

<400> SEQUENCE: 72

Gly Tyr Phe Ser Lys Ile Phe Arg Trp Ile Ala Gly Leu Phe Lys Arg
 1               5                  10                  15

Ile Gly

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Tyr Phe Ser Arg Ile Phe Arg Trp Ile Ala Gly Leu Phe Arg Trp
 1               5                  10                  15

Ile Gly

<210> SEQ ID NO 74
<211> LENGTH: 18
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 74

Gly Ile Arg Lys Phe Leu Gly Ser Ile Trp Arg Phe Ile Lys Ala Phe
 1               5                  10                  15

Tyr Gly

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ile Trp Lys Phe Leu Gly Ser Ile Arg Arg Phe Ile Lys Ala Phe
 1               5                  10                  15

Tyr Gly

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ile Gly Arg Phe Leu Lys Ser Ile Trp Gly Phe Ile Arg Ala Phe
 1               5                  10                  15

Tyr Lys

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Ile Arg Lys Phe Leu Gly Ser Ile Trp Arg Phe Ile Gly Ala Phe
 1               5                  10                  15

Tyr Lys

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ile Arg Lys Phe Leu Gly Ser Ile Trp Ala Phe Ile Arg Lys Phe
 1               5                  10                  15

Tyr Gly

<210> SEQ ID NO 79
<211> LENGTH: 18
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 79

Gly Ile Arg Lys Phe Leu Ser Gly Ile Trp Arg Phe Ile Lys Ala Phe
1               5                   10                  15

Tyr Gly

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Ile Arg Lys Phe Leu Ser Gly Ile Trp Arg Phe Ile Lys Ala Phe
1               5                   10                  15

Tyr Gly

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ile Trp Lys Phe Leu Ser Gly Ile Arg Arg Phe Ile Lys Ala Phe
1               5                   10                  15

Tyr Gly

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ile Arg Lys Phe Leu Gly Ala Ile Trp Arg Phe Ile Lys Ser Phe
1               5                   10                  15

Tyr Gly

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Tyr Phe Ala Arg Ile Phe Lys Trp Ile Ser Gly Leu Phe Arg Lys
1               5                   10                  15

Ile Gly

<210> SEQ ID NO 84
<211> LENGTH: 18
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 84

Gly Tyr Phe Ala Arg Ile Phe Lys Arg Ile Ser Gly Leu Phe Lys Trp
 1               5                   10                  15

Ile Gly

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Tyr Phe Ala Lys Ile Phe Gly Trp Ile Ser Lys Leu Phe Arg Gly
 1               5                   10                  15

Ile Gly

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Tyr Phe Ala Gly Ile Phe Arg Trp Ile Ser Arg Leu Phe Arg Gly
 1               5                   10                  15

Ile Gly

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Tyr Phe Lys Arg Ile Phe Ala Trp Ile Ser Gly Leu Phe Lys Arg
 1               5                   10                  15

Ile Gly

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Tyr Phe Ala Lys Ile Phe Arg Trp Ile Gly Ser Leu Phe Lys Arg
 1               5                   10                  15

Ile Gly

<210> SEQ ID NO 89
<211> LENGTH: 18
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 89

Gly Tyr Phe Ala Lys Ile Phe Arg Trp Ile Gly Ser Leu Phe Lys Arg
 1               5                  10                  15

Ile Gly

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Tyr Phe Lys Arg Ile Phe Arg Lys Ile Gly Ser Leu Phe Ala Trp
 1               5                  10                  15

Ile Gly

<210> SEQ ID NO 91
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ile Arg Lys Phe Leu Gly Ser Ile Trp Arg Phe Ile Arg Ala Phe
 1               5                  10                  15

Tyr Gly

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ile Trp Arg Phe Leu Gly Ser Ile Lys Arg Phe Ile Arg Ala Phe
 1               5                  10                  15

Tyr Gly

<210> SEQ ID NO 93
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ile Gly Arg Phe Leu Lys Ser Ile Trp Gly Phe Ile Arg Ala Phe
 1               5                  10                  15

Tyr Arg

<210> SEQ ID NO 94
<211> LENGTH: 18
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 94

Gly Ile Arg Arg Phe Leu Gly Ser Ile Trp Lys Phe Ile Gly Ala Phe
1               5                   10                  15

Tyr Arg

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ile Arg Arg Phe Leu Gly Ser Ile Trp Ala Phe Ile Lys Arg Phe
1               5                   10                  15

Tyr Gly

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ile Arg Arg Phe Leu Ser Gly Ile Trp Arg Phe Ile Lys Ala Phe
1               5                   10                  15

Tyr Gly

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ile Arg Lys Phe Leu Ser Gly Ile Trp Ala Phe Ile Arg Ala Phe
1               5                   10                  15

Tyr Gly

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ile Trp Arg Phe Leu Ser Gly Ile Lys Arg Phe Ile Arg Ala Phe
1               5                   10                  15

Tyr Gly

<210> SEQ ID NO 99
<211> LENGTH: 18
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 99

Gly Ile Arg Lys Phe Leu Gly Ala Ile Trp Arg Phe Ile Arg Ser Phe
1               5                   10                  15

Tyr Gly

<210> SEQ ID NO 100
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ile Trp Arg Phe Leu Gly Ala Ile Trp Lys Phe Ile Arg Ser Phe
1               5                   10                  15

Tyr Gly

<210> SEQ ID NO 101
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Tyr Phe Ala Arg Ile Phe Arg Trp Ile Ser Gly Leu Phe Lys Arg
1               5                   10                  15

Ile Gly

<210> SEQ ID NO 102
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Tyr Phe Ala Arg Ile Phe Arg Lys Ile Ser Gly Leu Phe Arg Trp
1               5                   10                  15

Ile Gly

<210> SEQ ID NO 103
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Tyr Phe Ala Arg Ile Phe Gly Trp Ile Ser Lys Leu Phe Arg Gly
1               5                   10                  15

Ile Gly

<210> SEQ ID NO 104
<211> LENGTH: 18
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 104

Lys Tyr Phe Ala Gly Ile Phe Arg Trp Ile Ser Arg Leu Phe Arg Gly
  1               5                  10                  15

Ile Gly

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Tyr Phe Lys Arg Ile Phe Ala Trp Ile Ser Gly Leu Phe Arg Arg
  1               5                  10                  15

Ile Gly

<210> SEQ ID NO 106
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Tyr Phe Ala Lys Ile Phe Arg Trp Ile Gly Ser Leu Phe Arg Arg
  1               5                  10                  15

Ile Gly

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Tyr Phe Ala Lys Ile Phe Arg Trp Ile Gly Ser Leu Phe Arg Arg
  1               5                  10                  15

Ile Gly

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Tyr Phe Arg Lys Ile Phe Arg Arg Ile Gly Ser Leu Phe Ala Trp
  1               5                  10                  15

Ile Gly

<210> SEQ ID NO 109
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 109

Gly Tyr Phe Ser Lys Ile Phe Arg Trp Ile Ala Gly Leu Phe Arg Arg
 1               5                  10                  15

Ile Gly

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Ile Arg Arg Ile Leu Gly Ser Phe Trp Arg Phe Phe Arg Ala Ile
 1               5                  10                  15

Tyr Gly

<210> SEQ ID NO 111
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Phe Arg Arg Ile Leu Gly Ser Phe Trp Arg Ile Phe Arg Ala Ile
 1               5                  10                  15

Tyr Gly

<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Phe Arg Arg Ile Leu Gly Ser Ile Trp Arg Phe Ile Arg Ala Phe
 1               5                  10                  15

Tyr Gly

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Ile Arg Arg Phe Leu Gly Ser Ile Trp Arg Ile Phe Arg Ala Phe
 1               5                  10                  15

Tyr Gly

<210> SEQ ID NO 114
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 114

Gly Ile Arg Arg Phe Leu Gly Ser Phe Trp Arg Ile Ile Arg Ala Phe
 1               5                  10                  15

Tyr Gly

<210> SEQ ID NO 115
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Leu Arg Arg Phe Ile Gly Ser Ile Trp Arg Phe Ile Arg Ala Phe
 1               5                  10                  15

Tyr Gly

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Leu Arg Arg Phe Ile Gly Ser Trp Arg Phe Ile Arg Ala Phe
 1               5                  10                  15

Tyr Gly

<210> SEQ ID NO 117
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Ile Arg Arg Phe Ile Gly Ser Ile Trp Arg Phe Leu Arg Ala Phe
 1               5                  10                  15

Tyr Gly

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Ile Arg Arg Phe Leu Gly Ser Phe Trp Arg Ile Phe Arg Ala Ile
 1               5                  10                  15

Tyr Gly

<210> SEQ ID NO 119
<211> LENGTH: 18
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 119

Gly Phe Arg Arg Phe Leu Gly Ser Phe Trp Arg Ile Ile Arg Ala Ile
 1               5                  10                  15

Tyr Gly

<210> SEQ ID NO 120
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ile Arg Arg Phe Leu Gly Ser Ile Tyr Arg Phe Ile Arg Ala Phe
 1               5                  10                  15

Trp Gly

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Ile Arg Arg Phe Tyr Gly Ser Ile Trp Arg Phe Ile Arg Ala Phe
 1               5                  10                  15

Leu Gly

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Tyr Ile Ala Arg Phe Ile Arg Trp Phe Ser Gly Leu Ile Arg Arg
 1               5                  10                  15

Phe Gly

<210> SEQ ID NO 123
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Tyr Gly Ala Arg Ile Phe Arg Trp Ile Ser Gly Leu Ile Arg Arg
 1               5                  10                  15

Phe Gly

<210> SEQ ID NO 124
<211> LENGTH: 18
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 124

Gly Tyr Phe Ala Arg Phe Ile Arg Trp Ile Ser Gly Leu Phe Arg Arg
 1               5                  10                  15

Ile Gly

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Tyr Phe Ala Arg Ile Phe Arg Trp Ile Ser Gly Ile Phe Arg Arg
 1               5                  10                  15

Leu Gly

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Tyr Ile Ala Arg Ile Phe Arg Trp Phe Ser Gly Leu Phe Arg Arg
 1               5                  10                  15

Ile Gly

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Leu Arg Arg Phe Ile Gly Ser Leu Trp Arg Phe Leu Arg Ala Phe
 1               5                  10                  15

Tyr Gly

<210> SEQ ID NO 128
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Tyr Phe Ala Arg Leu Phe Arg Trp Leu Ser Gly Ile Phe Arg Arg
 1               5                  10                  15

Leu Gly

<210> SEQ ID NO 129
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 129

Gly Ile Arg Arg Phe Leu Gly Ser Leu Trp Arg Phe Leu Arg Ala Phe
 1               5                  10                  15

Tyr Gly

<210> SEQ ID NO 130
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Tyr Phe Ala Arg Leu Phe Arg Trp Leu Ser Phe Leu Phe Arg Arg
 1               5                  10                  15

Ile Gly

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Leu Arg Arg Phe Leu Gly Ser Ile Trp Arg Phe Leu Arg Ala Phe
 1               5                  10                  15

Tyr Gly

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Tyr Phe Ala Arg Leu Phe Arg Trp Ile Ser Gly Leu Phe Arg Arg
 1               5                  10                  15

Leu Gly

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Ile Arg Arg Phe Tyr Gly Ser Ile Trp Arg Phe Ile Arg
 1               5                  10

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 134

Arg Ile Phe Arg Trp Ile Ser Gly Tyr Phe Arg Ile Gly
 1               5                  10

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Arg Phe Tyr Gly Ser Ile Trp Arg Phe Ile Arg Ala Phe
 1               5                  10

<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Phe Ala Arg Ile Phe Arg Trp Ile Ser Gly Tyr Phe Arg Arg
 1               5                  10

<210> SEQ ID NO 137
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Leu Arg Arg Phe Tyr Gly Ser Leu Trp Arg Phe Leu Arg
 1               5                  10

<210> SEQ ID NO 138
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Leu Phe Arg Trp Leu Ser Gly Tyr Phe Arg Leu Gly
 1               5                  10

<210> SEQ ID NO 139
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Arg Phe Tyr Gly Ser Leu Trp Arg Phe Leu Arg Ala Phe
 1               5                  10

<210> SEQ ID NO 140
<211> LENGTH: 14
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 140

Phe Ala Arg Leu Phe Arg Trp Leu Ser Gly Tyr Phe Arg Arg
 1               5                  10

<210> SEQ ID NO 141
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Ile Arg Arg Phe Tyr Gly Ser Ile Trp Arg Phe Leu Arg
 1               5                  10

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Leu Phe Arg Trp Ile Ser Gly Tyr Phe Arg Arg Ile Gly
 1               5                  10

<210> SEQ ID NO 143
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Arg Arg Phe Tyr Gly Ser Ile Trp Arg Phe Leu Arg Ala Phe
 1               5                  10

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Phe Ala Arg Leu Phe Arg Trp Ile Ser Gly Tyr Phe Arg Arg
 1               5                  10

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Ile Arg Arg Phe Tyr Gly Ser Leu Trp Arg Phe Leu Arg
 1               5                  10

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Arg Leu Phe Arg Trp Ile Ser Gly Tyr Phe Arg Arg Leu Gly
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Arg Arg Phe Tyr Gly Ser Ile Trp Arg Phe Leu Arg Ala Phe
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Phe Ala Arg Ile Phe Arg Trp Leu Ser Gly Tyr Phe Arg Arg
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Phe Arg Arg Ile Tyr Gly Ser Ile Trp Arg Phe Ile Arg
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Ile Arg Arg Phe Tyr Gly Ser Ile Trp Arg Ile Phe Arg
1               5                   10

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Arg Phe Ile Arg Trp Ile Ser Gly Tyr Phe Arg Arg Ile Gly
1               5                   10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Ile Phe Arg Trp Ile Ser Gly Tyr Ile Arg Arg Phe Gly
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Arg Ile Phe Arg Trp Ile Ser Gly Tyr Phe Arg Arg Leu Gly
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Leu Phe Arg Trp Ile Ser Gly Tyr Phe Arg Arg Ile Gly
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Ile Arg Arg Phe Tyr Gly Ser Ile Trp Arg Phe Leu Arg
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Leu Arg Arg Phe Tyr Gly Ser Ile Trp Arg Phe Ile Arg
1               5                   10

<210> SEQ ID NO 157
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 157

Gly Ile Arg Arg Phe Tyr Gly Ser Leu Trp Arg Phe Ile Arg
 1               5                  10

<210> SEQ ID NO 158
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Ile Arg Arg Tyr Phe Gly Ser Ile Trp Arg Phe Ile Arg
 1               5                  10

<210> SEQ ID NO 159
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Ile Arg Arg Tyr Phe Gly Ser Ile Trp Arg Phe Leu Arg
 1               5                  10

<210> SEQ ID NO 160
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Ile Arg Arg Tyr Phe Gly Ser Leu Trp Arg Phe Ile Arg
 1               5                  10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Ile Phe Arg Trp Ile Ser Gly Phe Tyr Arg Arg Ile Gly
 1               5                  10

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Arg Leu Phe Arg Trp Ile Ser Gly Phe Tyr Arg Arg Leu Gly
 1               5                  10

<210> SEQ ID NO 163
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Ile Phe Arg Trp Leu Ser Gly Phe Tyr Arg Arg Ile Gly
 1               5                  10

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Arg Leu Phe Arg Trp Leu Ser Gly Phe Tyr Arg Arg Ile Gly
 1               5                  10

<210> SEQ ID NO 165
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Phe Leu Arg Trp Ile Ser Gly Tyr Phe Arg Arg Ile Gly
 1               5                  10

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Phe Leu Arg Trp Ile Ser Gly Phe Tyr Arg Arg Ile Gly
 1               5                  10

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Phe Arg Arg Leu Tyr Gly Ser Ile Trp Arg Phe Ile Arg
 1               5                  10

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Ile Arg Arg Phe Tyr Gly Ser Ile Trp Arg Ile Phe Arg
```

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 169

Gly Ile Lys Arg Phe Tyr Gly Ser Ile Trp Arg Phe Ile Arg
 1               5                  10

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 170

Arg Ile Phe Arg Trp Ile Ser Gly Tyr Phe Arg Lys Ile Gly
 1               5                  10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 171

Arg Lys Phe Tyr Gly Ser Ile Trp Arg Phe Ile Arg Ala Phe
 1               5                  10

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 172

Phe Ala Arg Ile Phe Arg Trp Ile Ser Gly Tyr Phe Lys Arg
 1               5                  10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 173

Gly Leu Lys Arg Phe Tyr Gly Ser Leu Trp Arg Phe Leu Arg
 1               5                  10

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

```
<400> SEQUENCE: 174

Arg Leu Phe Arg Trp Leu Ser Gly Tyr Phe Arg Lys Leu Gly
 1               5                   10

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Lys Phe Tyr Gly Ser Leu Trp Arg Phe Leu Arg Ala Phe
 1               5                   10

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Phe Ala Arg Leu Phe Arg Trp Leu Ser Gly Tyr Phe Lys Arg
 1               5                   10

<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Ile Lys Arg Phe Tyr Gly Ser Ile Trp Arg Phe Leu Arg
 1               5                   10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Leu Phe Arg Trp Ile Ser Gly Tyr Phe Arg Lys Ile Gly
 1               5                   10

<210> SEQ ID NO 179
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Lys Phe Tyr Gly Ser Ile Trp Arg Phe Leu Arg Ala Phe
 1               5                   10

<210> SEQ ID NO 180
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 180

Phe Ala Arg Leu Phe Arg Trp Ile Ser Gly Tyr Phe Lys Arg
 1               5                  10

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Ile Arg Lys Phe Tyr Gly Ser Leu Trp Arg Phe Leu Arg
 1               5                  10

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Leu Phe Lys Trp Ile Ser Gly Tyr Phe Arg Arg Leu Gly
 1               5                  10

<210> SEQ ID NO 183
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Arg Phe Tyr Gly Ser Ile Trp Arg Phe Leu Lys Ala Phe
 1               5                  10

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Phe Ala Lys Ile Phe Arg Trp Leu Ser Gly Tyr Phe Arg Arg
 1               5                  10

<210> SEQ ID NO 185
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Phe Arg Arg Ile Tyr Gly Ser Ile Trp Arg Phe Ile Lys
 1               5                  10
```

```
<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Ile Arg Lys Phe Tyr Gly Ser Ile Trp Arg Ile Phe Arg
 1               5                  10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Arg Phe Ile Arg Trp Ile Ser Gly Tyr Phe Arg Lys Ile Gly
 1               5                  10

<210> SEQ ID NO 188
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Ile Phe Lys Trp Ile Ser Gly Tyr Ile Arg Arg Phe Gly
 1               5                  10

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Ile Phe Arg Trp Ile Ser Gly Tyr Phe Arg Lys Leu Gly
 1               5                  10

<210> SEQ ID NO 190
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Lys Leu Phe Arg Trp Ile Ser Gly Tyr Phe Arg Arg Ile Gly
 1               5                  10

<210> SEQ ID NO 191
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191
```

```
Gly Ile Arg Arg Phe Tyr Gly Ser Ile Trp Lys Phe Leu Arg
 1               5                  10

<210> SEQ ID NO 192
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Leu Lys Arg Phe Tyr Gly Ser Ile Trp Arg Phe Ile Arg
 1               5                  10

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Ile Arg Arg Phe Tyr Gly Ser Leu Trp Lys Phe Ile Arg
 1               5                  10

<210> SEQ ID NO 194
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Ile Arg Arg Tyr Phe Gly Ser Leu Trp Arg Phe Ile Arg
 1               5                  10

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Leu Arg Arg Tyr Phe Gly Ser Ile Trp Arg Phe Leu Arg
 1               5                  10

<210> SEQ ID NO 196
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Ile Arg Arg Tyr Phe Ser Gly Leu Trp Arg Phe Ile Arg
 1               5                  10

<210> SEQ ID NO 197
<211> LENGTH: 14
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 197

Arg Phe Leu Arg Trp Ile Ser Gly Phe Tyr Arg Arg Ile Gly
 1               5                  10

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Arg Leu Phe Arg Trp Ile Ser Gly Phe Tyr Arg Arg Leu Gly
 1               5                  10

<210> SEQ ID NO 199
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Phe Leu Arg Trp Leu Ser Gly Phe Tyr Arg Arg Ile Gly
 1               5                  10

<210> SEQ ID NO 200
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Leu Ile Arg Trp Leu Ser Gly Phe Tyr Arg Arg Phe Gly
 1               5                  10

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Phe Leu Arg Trp Phe Ser Gly Tyr Ile Arg Arg Ile Gly
 1               5                  10

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Phe Leu Arg Trp Ile Ser Gly Tyr Phe Arg Arg Ile Gly
 1               5                  10

<210> SEQ ID NO 203

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Phe Arg Arg Leu Tyr Ser Gly Ile Trp Arg Phe Ile Arg
 1               5                  10

<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Ile Arg Arg Tyr Phe Gly Ser Ile Trp Arg Ile Phe Arg
 1               5                  10

<210> SEQ ID NO 205
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Ile Arg Arg Phe Leu Gly Trp Ile Arg Ala Phe Ile Ser Arg Phe
 1               5                  10                  15

Val Gly Arg

<210> SEQ ID NO 206
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: DiMe-Lys
<220> FEATURE:
<221> NAME/KEY: MOD_RES
<222> LOCATION: (10)
<223> OTHER INFORMATION: DiMe-Lys
<220> FEATURE:
<221> NAME/KEY: MOD_RES
<222> LOCATION: (15)
<223> OTHER INFORMATION: DiMe-Lys

<400> SEQUENCE: 206

Gly Ile Lys Lys Phe Leu Gly Trp Ile Lys Ala Phe Ile Ser Lys Phe
 1               5                  10                  15

Val Gly

<210> SEQ ID NO 207
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)
<223> OTHER INFORMATION: DiMe-Lys
<220> FEATURE:
<221> NAME/KEY: MOD_RES
<222> LOCATION: (10)
<223> OTHER INFORMATION: DiMe-Lys

<400> SEQUENCE: 207

Gly Ile Lys Arg Phe Leu Gly Trp Ile Lys Ala Phe Ile Ser Arg Phe
 1               5                  10                  15

Val Gly

<210> SEQ ID NO 208
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Gly, Thr, Ser or Ala
<220> FEATURE:
<221> NAME/KEY: MOD_RES
<222> LOCATION: (2)
<223> OTHER INFORMATION: any hydrophobic amino acid
<220> FEATURE:
<221> NAME/KEY: MOD_RES
<222> LOCATION: (5)..(6)
<223> OTHER INFORMATION: any hydrophobic amino acid
<220> FEATURE:
<221> NAME/KEY: MOD_RES
<222> LOCATION: (7)..(8)
<223> OTHER INFORMATION: Gly, Thr, Ser or Ala
<220> FEATURE:
<221> NAME/KEY: MOD_RES
<222> LOCATION: (9)..(10)
<223> OTHER INFORMATION: any hydrophobic amino acid
<220> FEATURE:
<221> NAME/KEY: MOD_RES
<222> LOCATION: (12)..(13)
<223> OTHER INFORMATION: any hydrophobic amino acid
<220> FEATURE:
<221> NAME/KEY: MOD_RES
<222> LOCATION: (15)
<223> OTHER INFORMATION: Gly, Thr, Ser or Ala
<220> FEATURE:
<221> NAME/KEY: MOD_RES
<222> LOCATION: (16)..(17)
<223> OTHER INFORMATION: any hydrophobic amino acid
<220> FEATURE:
<221> NAME/KEY: MOD_RES
<222> LOCATION: (18)
<223> OTHER INFORMATION: Gly, Thr, Ser or Ala

<400> SEQUENCE: 208

Xaa Xaa Arg Arg Xaa Xaa Xaa Xaa Xaa Arg Xaa Xaa Arg Xaa Xaa
 1               5                  10                  15

Xaa Xaa

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: any hydrophobic amino acid
<220> FEATURE:
<221> NAME/KEY: MOD_RES
```

```
<222> LOCATION: (5)..(6)
<223> OTHER INFORMATION: Gly, Thr, Ser or Ala
<220> FEATURE:
<221> NAME/KEY: MOD_RES
<222> LOCATION: (7)..(8)
<223> OTHER INFORMATION: any hydrophobic amino acid
<220> FEATURE:
<221> NAME/KEY: MOD_RES
<222> LOCATION: (10)..(11)
<223> OTHER INFORMATION: any hydrophobic amino acid
<220> FEATURE:
<221> NAME/KEY: MOD_RES
<222> LOCATION: (13)
<223> OTHER INFORMATION: Gly, Thr, Ser or Ala
<220> FEATURE:
<221> NAME/KEY: MOD_RES
<222> LOCATION: (14)
<223> OTHER INFORMATION: any hydrophobic amino acid

<400> SEQUENCE: 209

Arg Arg Xaa Xaa Xaa Xaa Xaa Xaa Arg Xaa Xaa Arg Xaa Xaa
  1               5                  10

<210> SEQ ID NO 210
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Gly, Thr, Ser or Ala
<220> FEATURE:
<221> NAME/KEY: MOD_RES
<222> LOCATION: (2)
<223> OTHER INFORMATION: any hydrophobic amino acid
<220> FEATURE:
<221> NAME/KEY: MOD_RES
<222> LOCATION: (5)..(6)
<223> OTHER INFORMATION: any hydrophobic amino acid
<220> FEATURE:
<221> NAME/KEY: MOD_RES
<222> LOCATION: (7)..(8)
<223> OTHER INFORMATION: Gly, Thr, Ser or Ala
<220> FEATURE:
<221> NAME/KEY: MOD_RES
<222> LOCATION: (9)..(10)
<223> OTHER INFORMATION: any hydrophobic amino acid
<220> FEATURE:
<221> NAME/KEY: MOD_RES
<222> LOCATION: (12)..(13)
<223> OTHER INFORMATION: any hydrophobic amino acid

<400> SEQUENCE: 210

Xaa Xaa Arg Arg Xaa Xaa Xaa Xaa Xaa Xaa Arg Xaa Xaa Arg
  1               5                  10
```